United States Patent
Yarden et al.

(10) Patent No.: US 10,458,908 B2
(45) Date of Patent: Oct. 29, 2019

(54) SYSTEM AND METHOD FOR QUALIFYING PLANT MATERIAL

(71) Applicant: GemmaCert Ltd., Ra'anana (IL)

(72) Inventors: Dana Yarden, Tel Aviv (IL); Oded Shoseyov, Shoham (IL); Merav Blanca, Modiin (IL)

(73) Assignee: Gemmacert Ltd., Ra'anana (IL)

(*) Notice: Subject to any disclaimer, the term of this patent is extended or adjusted under 35 U.S.C. 154(b) by 0 days.

(21) Appl. No.: 16/075,518

(22) PCT Filed: Feb. 2, 2017

(86) PCT No.: PCT/IL2017/050130
§ 371 (c)(1),
(2) Date: Aug. 3, 2018

(87) PCT Pub. No.: WO2017/134669
PCT Pub. Date: Aug. 10, 2017

(65) Prior Publication Data
US 2019/0033210 A1  Jan. 31, 2019

Related U.S. Application Data

(60) Provisional application No. 62/291,060, filed on Feb. 4, 2016.

(51) Int. Cl.
*G01N 21/359* (2014.01)
*G01N 33/00* (2006.01)
*G01N 21/65* (2006.01)

(52) U.S. Cl.
CPC .......... *G01N 21/359* (2013.01); *G01N 21/65* (2013.01); *G01N 33/0098* (2013.01); *G01N 2201/129* (2013.01)

(58) Field of Classification Search
CPC .. G01N 21/359; G01N 33/0098; G01N 21/65; G01N 2201/129
See application file for complete search history.

(56) References Cited

U.S. PATENT DOCUMENTS

| | | | |
|---|---|---|---|
| 2004/0130714 A1* | 7/2004 | Gellerman | G01J 3/44 356/300 |
| 2011/0089323 A1* | 4/2011 | Treado | G01J 3/02 250/330 |

(Continued)

FOREIGN PATENT DOCUMENTS

EP  2 107 361  10/2009

OTHER PUBLICATIONS

International Search Report and Written Opinion of the International Searching Authority from the Israel Patent Office for International Application No. PCT/IL2017/050130, dated Jun. 1, 2017 (8 pages).

(Continued)

*Primary Examiner* — Hina F Ayub
(74) *Attorney, Agent, or Firm* — Dekel Patent Ltd.; David Klein

(57) ABSTRACT

System and methods may qualify plant material. A system for qualifying plant material may include an inspection zone, a support stage configured to support the plant material in the inspection zone, at least one camera configured to acquire at least one image of the plant material in the inspection zone, at least one processor configured to receive and analyze the camera image to identify a region of interest containing specific plant structures possessing active component, and at least one spectrometer configured to acquire a spectrometric measurement of the plant material in the inspection zone. The at least one processor may be further configured to facilitate a spectrometric measurement of the specific plant structures identified in the camera image, and (Continued)

to enable output of an indicator of a quality measure of the plant material based on the spectrometric measurement of the specific plant structures identified in the camera image.

20 Claims, 17 Drawing Sheets

(56) References Cited

U.S. PATENT DOCUMENTS

2016/0139055 A1  5/2016  Pierce, III et al.
2017/0118925 A1* 5/2017  Noguchi ................ G06Q 50/02
2018/0306827 A1* 10/2018 Pierce, III .............. G01N 21/84

OTHER PUBLICATIONS

American Herbal Pharmacopoeia, cannabis inflorescence, standards of identity, Analysis and quality control, 15 pages, (2013).
I. Azaria.; N. Goldshleger.et al.; "Detection of Cannabis Plants by Hyper-Spectral Remote Sensing Means". Tel Aviv University Publication, Horizons in Geography, vol. 77, pp. 59-73, (2011).
C. M. Bishop; "Pattern Recognition and Machine Learning". Springer, pp. 1-738 (2006).
Chen et al.; "A Review of Non-destructive Methods for Quality Evaluation and Sorting of Agricultural Products.", J. agric. Engng Res. vol. 49, pp. 85-98, (1991).
DeBacker B et al.; "Innovative development and validation of an HPLC/DAD method for the qualitative and quantitative determination of major cannabinoids in cannabis plants materials.", J Chromatogr B, vol. 877, 4115-4124, (2009).
Fahlgren et al.; "Lights, camera, action: high-throughput plant phenotyping is ready for a close-up", Current opinion in plant biology, vol. 24, pp. 93-99 (2015).
Failmezger, et al. "Semi-automated 3D leaf reconstruction and analysis of trichome patterning from light microscopic images.", PloS Comput Biol. vol. 9, Issue 4, pp. 1-10, (2013).
Garbacik et al.; "In planta imaging of delta 9-tetrahydrocannabinolic acid in *Cannabis sativa* L. with hyperspectral coherent anti-Stokes Raman scattering microscopy." Journal of biomedical optics vol. 18, Issue 4, pp. 046009-1 to 046009-5, (2013).
Hans Grahn et al; "Techniques and Applications of Hyperspectral Image Analysis". John Wiley & Sons, 9 pages, (2007).
Z. Haddi et al; "A portable electronic nose system for the identification of cannabis-based drugs.", Sensors and Actuators B: Chemical, vol. 155, Issue 2, SPMI-GC-MS, pp. 456-463, (2011).
Ilias, Y. et al; Extraction and analysis of different Cannabis samples by headspace solid-phase microextraction combined with gas chromatography-mass spectrometry. J. Sep. Science, pp. 2293-2300, (2005).
Higgins, Kevin; "Five New Technologies for Inspection". Food Processing,pp. 1-5, (2013).
Neilson et al.; "Utilization of a high-throughput shoot imaging system to examine the dynamic phenotypic responses of a C4 cereal crop plant to nitrogen and water deficiency over time." Journal of experimental botany, pp. 1817-1832, (2015).
Analytical Monograph Cannabis Flos (flowers / granulated) OMC /Farmalyse BV Version 7.1, 01 pages, (2014).
Shepherd et al.; "Infrared spectroscopy enabling an evidence-based diagnostic surveillance approach to agricultural and environmental management in developing countries"., J. Near Infrared Spectrosc. vol. 15, pp. 1-19, (2007).
Swift W et al.; "Analysis of cannabis seizures in NSW, Australia, cannabis potency and cannabinoid profile.", PLOS ONE, vol. 8, Issue 7, pp. 1-9, (2013).
United Nations New York, Laboratory and Scientific Section UN Office on Drugs and Crime Vienna (2009) "Recommended Methods for the Identification and Analysis of Cannabis and Cannabis Products", Manual for use by National Drug Analysis Laboratories, 56 pages, (2009).
Wernick et al.; "Machine Learning in Medical Imaging", IEEE Signal Processing Magazine 27 (4): pp. 25-38, (2010).
Wikipedia, Hyperspectral Imaging, available at: https://wiki2.org/en/Hyperspectral_imaging 915 pages).

* cited by examiner

```
┌─────────────────────────────────────────────────────────────────┐
│ PROVIDING SAMPLE SET OF PLANT MATERIAL ELEMENTS 2010            │
└─────────────────────────────────────────────────────────────────┘

┌─────────────────────────────────────────────────────────────────┐
│ COLLECTING IMAGE DATA OF THE SET ELEMENT 2020                   │
└─────────────────────────────────────────────────────────────────┘

┌─────────────────────────────────────────────────────────────────┐
│ DETERMINING STRUCTURAL PARAMETERS BASED ON THE IMAGE DATA       │
│ 2025                                                            │
└─────────────────────────────────────────────────────────────────┘

┌─────────────────────────────────────────────────────────────────┐
│ COLLECTING SPECTROMETRIC DATA OF THE SET ELEMENTS 2030          │
└─────────────────────────────────────────────────────────────────┘

┌─────────────────────────────────────────────────────────────────┐
│ PROCESSING THE SET ELEMENTS AND PERFORMING ANALYTICAL           │
│ MEASURMMENTS FOR ACTIVE MATERIALS 2040                          │
└─────────────────────────────────────────────────────────────────┘

┌─────────────────────────────────────────────────────────────────┐
│ DETERMINING PREDICTED ACTIVE MATERIAL TRACES IN                 │
│ SPECTROMETRIC 2050                                              │
└─────────────────────────────────────────────────────────────────┘

┌─────────────────────────────────────────────────────────────────┐
│ DETERMINING QUANTITATIVE FACTOR OF ACTIVE MATERIALS BASED       │
│ ON STRUCTURAL PARAMETERS 2060                                   │
└─────────────────────────────────────────────────────────────────┘

┌─────────────────────────────────────────────────────────────────┐
│ CORRELATING PREDICTED CONTENT WITH ANALYTICALLY MEASURED        │
│ CONTENT 2070                                                    │
└─────────────────────────────────────────────────────────────────┘

┌─────────────────────────────────────────────────────────────────┐
│ DETERMINING DATABASE INCLUDING BEING WEIGHTING FACTORS $f_j^s(d)$│
│ FOR ACTIVE MATERIALS BASED ON STRUCTURAL PARAMETERS FOR         │
│ ACTIVE MATERIALS 2080                                           │
└─────────────────────────────────────────────────────────────────┘
```

FIG. 4

SYSTEM AND METHOD FOR QUALIFYING PLANT MATERIAL

This application is the national stage of International Application No. PCT/IL2017/050130, filed Feb. 2, 2017, which claims the benefit of priority of U.S. Provisional Application No. 62/291,060, filed Feb. 4, 2016. All of the foregoing applications are incorporated herein by reference in their entirety.

TECHNOLOGICAL FIELD

The present invention relates to a system for qualifying plant material and to a method of using same. The invention relates specifically to qualification of plants containing one or more active materials.

BACKGROUND ART

References considered to be relevant as background to the presently disclosed subject matter are listed below:

1. I. Azaria.; N. Goldshleger.; E. Ben-Dor.; R. Bar-Hamburger "Detection of Cannabis Plants by Hyper-Spectral Remote Sensing Means". Tel Aviv University Publication, Horizons in Geography, 2011, Vol. 77, pp. 59-73.
2. K. D Shepherd.; M. G. Walsh (2007) "Infrared spectroscopy enabling an evidence-based diagnostic surveillance approach to agricultural and environmental management in developing countries". J. Near Infrared Spectrosc. 15: 1-19.
3. Hans Grahn; Paul Geladi (2007). "Techniques and Applications of Hyperspectral Image Analysis". John Wiley & Sons.
4. Higgins, Kevin (2013). "Five New Technologies for Inspection". Food Processing
5. Wernick, Yang.; Brankov.; Yourganov Strother (2010) "Machine Learning in Medical Imaging". IEEE Signal Processing Magazine 27 (4): 25-38.
6. C. M. Bishop (2006). "Pattern Recognition and Machine Learning". Springer.
7. United Nations New York, Laboratory and Scientific Section UN Office on Drugs and Crime Vienna (2009) "Recommended Methods for the Identification and Analysis of Cannabis and Cannabis Products" Manual for use by National Drug Analysis Laboratories.
8. Analytical Monograph Cannabis Flos (flowers/granulated) OMC/Farmalyse BV Version 7.1/Nov. 28, 2014
9. Swift W, Wong A, Li K M, Arnold J C, McGregor L S, 2013, Analysis of cannabis seizures in NSW, Australia, cannabis potency and cannabinoid profile. PLOS ONE 8: e70052.
10. DeBacker B, Debrus B, Lebrun P, Theunis L, Dubios N, Decock L, Verstraete A, Hubert P, Charlier C, 2009, Innovative development and validation of an HPLC/DAD method for the qualitative and quantitative determination of major cannabinoids in cannabis plants materials. J Chromatogr B, 877, 4115-24
11. American Herbal Pharmacopoeia, cannabis inflorescence, standards of identity, Analysis and quality control, 2013

Acknowledgement of the above references herein is not to be inferred as meaning that these are in any way relevant to the patentability of the presently disclosed subject matter.

BACKGROUND

Chemical analysis of whole plants, plant parts or processed plant tissue is routinely used to identify phenotypes that are important for identifying or developing crop plants of higher yield or nutritional value, plants resistant to stress (e.g. salt, temperature) or pathogens, or plants used for medicinal or recreational purposes.

A non-destructive technique to assess the quality of a plant material is described in EP2107361. According to this technique, the quality of the plant material is determined by detecting changes in the colour of plant material, namely by illuminating the sample with light consisting of two additive primary colours, and recording colour parameter(s) from the illuminated sample.

One example of a plant used for medicinal and recreational purposes is cannabis. In recent years, use of cannabis in the adult population has dramatically increased due to legalization of cannabis in parts of the United States and use of cannabis or cannabis extracts as palliative medication.

The active ingredients of cannabis plants are the cannabinoids, a class of diverse chemical compounds that act on cannabinoid receptors in cells that repress neurotransmitter release in the brain.

The primary and most well-known cannabinoid is phytocannabinoid tetrahydrocannabinol (THC), while cannabidiol (CBD), which is another cannabinoid, is known to be the primary analgesic compounds of cannabis. In addition, there are at least 85 additional plant cannabinoids having varied physiological effects.

Desirable traits of recreational cannabis include high levels of THC and low levels of CBD and Cannabinol (CBN). Medical cannabis is often characterized by higher levels of CBD and lower levels of THC. The therapeutic CBD is desirable for medicinal effect but the psychoactive THC may be unnecessary and undesirable for some patients. Medicinal effects of cannabis include reduced symptoms such as nausea, seizures, eye pressure and pain.

Several approaches are presently used to categorize types of cannabis plant material for recreational and medicinal use. Most of these approaches utilize processed (e.g. ground and extracted, or thermally decomposed) plant tissue for quantification of cannabinoids, and primarily of THC and CBD.

Gas Chromatography (GC) is the most commonly used approach for quantitation of plant cannabinoids. This approach thermally decomposes the samples for analysis which leads to decarboxylation of the acidic cannabinoid. Since GC requires thermal modification of cannabinoid acids for detection, it is less effective in detecting some cannabinoid species and as such considered to be an incomplete approach.

High Performance Liquid Chromatography (HPLC) is another approach for quantifying cannabinoids in processed plant material. HPLC is advantageous in that it identifies the neutral forms of CBDA and THCA extracted from processed cannabis tissue. HPLC is highly reproducible for different cannabis strains due to the availability of reference standards and the lack of need for decarboxylation for detection.

Although the above described approaches can be used to categorize cannabis strains according to THC and CBD quantities, they require processed plants material and are time consuming and as such are inappropriate for screening and sorting whole plant material (whole plant or whole plant parts such as flowers).

Approaches for quantifying cannabinoids in whole plants or plant parts have been proposed, e.g. electronic nose based on the use of commercially available metal oxide gas sensors to classify different types of drugs (Z. Haddi et al, A portable electronic nose system for the identification of cannabis-based drugs. Sensors and Actuators B: Chemical, Volume 155, Issue 2, 20 Jul. 2011, Pages 456-463), SPMI-GC-MS; Ilias, Y. et al, Extraction and analysis of different Cannabis samples by headspace solid-phase microextraction combined with gas chromatography-mass spectrometry. J. Sep. Science, 15 Nov. 2005, 2293-2300. However, such approaches are less accurate and reproducible than the destructive approaches described above.

GENERAL DESCRIPTION

There is a need in the art for a novel approach for qualifying plant materials. In particular, there is a need for a non-destructive technique that can accurately and rapidly quantify active ingredients in whole (unprocessed) plants material and thus be used in classifying (and possibly sorting) plant material such as flowers from cannabis plants.

The present invention provides a method and system for non-destructive automatic inspection of whole plants material. The technique of the present invention can be applied to such plant materials in a production line scheme (e.g. while progressing on production line) enabling immediate inspection/qualification and classification of individual plants in accordance with one or more categories or quality measures.

According to some embodiments, the invention may be used for inspecting and classifying flowers from cannabis plants, and is therefore described below with respect to this specific application. However, it should be understood that the principles of the invention are not limited to this specific application.

It should be understood that, for the purposes of the present application, the term "plant material" or "plant material element" as interchangeably used herein refers to whole plant material or part of the whole plant material in its natural unprocessed phase (such as flower, inflorescence, leaf, or any plant material including a seed). Considering cannabis, its natural unprocessed phase is flower or a plant section (branch) including one or more flowers. The term "non-destructive" thus relates to both, the plant phase to which inspection is applied and the type of inspection, to distinguish it from destructive type utilizing chemical probes.

The technique of the present invention utilizes collection/measurement of image data (e.g. visible light image data) in combination with collection/measurement of spectroscopic data from the same plant material (e.g. the same region(s) of the plant material) for categorizing the plant material by determining "correlation" between the spectroscopic data and the visible image data of the plant. More specifically, according to the present invention, the measured image data is used (undergoes image processing) to determine one or more structural parameters in the region(s) of the plant material (identify location, quantity and/or density of pre-determined plant structures associated with one or more active materials of the plant, as will be described in more details further below). The data about the predetermined plant structures is used for "calibrating" the spectroscopic data and determine measure(s) of one or more selected active materials of the plant. Such measure may be determined in weight percentage (%), total amount in mg, or any other measure suitable for the selected active material(s).

In this connection, the terms active material, active component and active ingredient as used herein interchangeably should be interpreted broadly as any material of interest that might be used for characterizing the plant material. In the specific example of cannabis plants, such active materials include various cannabinoids. Alternatively or additionally, such active materials may be various types of sugar, caffeine, and in particular terpenes phenol-based compounds, or any other material that is used for categorizing selected plants.

Utilizing the image data of the at least a region of the plant material in correlation with the spectroscopic data of the same at least region of the plant material enables categorizing/classifying the plant material (e.g. leaves, flowers, fruits, etc.) with respect to specific one or more predefined categories defined by the quality measure(s), e.g. content of one or more active ingredients in the plant material. Additionally, each element, such as leaf, flower, seed or fruit, may be provided (assigned) with tagging data indicative of the specific category (active material composition thereof). This enables to provide users with additional data as well as enables collection of corresponding data about effects of specific plants. Such data about plant's effects on users may be correlated with other parameters of the specific plant (e.g. spectroscopic data) to provide additional information about the active materials of the plant.

It should be noted that the terms "categorization", "classification" and "sorting" are used herein interchangeably and refer to creation of classification data (or sorting data) about the plant material (i.e. creation of data indicative of the quality measure(s) of the plant material), which can be used for physical sorting of the plant material and/or tagging (e.g. labeling) the plant material. In this connection, it should be understood that the term "tagging the plant material" signifies creation of tagging data associating the plant material and its respective classification data; the tagging data may be stored in a memory and/or used for physically labelling/tagging the plant material and/or a package thereof.

As indicated above, active ingredients of cannabis plants are the cannabinoids. Cannabinoids are typically concentrated in specialized glandular structures called trichomes, which cover the surface of the leaves, seeds and especially the flowers of the cannabis plants. Trichomes exist in many shapes and sizes, but there are three that appear most often on cannabis plants: (1) bulbous trichomes, which are the smallest of the bunch (bulbous trichomes are as small as 10-15 micrometers, which is tiny enough to only be comprised of a handful of cells), and appear on the surface of the entire plant; (2) Capitate sessile trichomes which are slightly larger, contain both a head and a stalk, and are quite a bit more abundant than their bulbous brethren, but cannot hold a candle to the bountifulness and size of the third trichome variety; and (3) Capitate-stalked trichomes which range from anywhere between 50-100 mm wide, i.e. are much larger and can actually be seen by the naked eye, and which have a structure consisting of a stalk comprised of epidermal and hypodermic feels that build up to a basal cell which attaches to a large gland head. This gland head, held together by a waxy cuticle layer, serves as the epicenter for cannabinoid and terpenoid synthesis. Although all three types of trichomes produce cannabinoids, they are different in type and quantity of cannabinoids produced. The capitate-stalked trichomes appear in abundance in and around to the calyxes of budding flowers, producing the highest concentration of essential oils due to their size. Cannabinoid synthesis within the trichomes begins as cannabis plants move into their bloom phase. As they begin to produce flowers, trichomes form along the outer surface of the above-ground plant vegetation and begin to transport vacuoles and plastids from their stalk into the gland head. At this point, cells within the gland head will begin to metabolize and form precursors for what will eventually become cannabinoids.

Thus, according to one broad aspect, the present invention provides a system for determining a quality measure of a plant material, the system comprising:

(a) an optical inspection unit configured and operable for applying optical inspection to at least one region of the plant material and generating measured image data and spectroscopic data of said at least one region of the plant material; and (b) a control unit comprising an analyzer utility configured and operable for receiving the measured image data and the measured spectroscopic data of the at least one region of the plant material, analyzing the measured image data to determine at least one structural parameter of the plant material, determining one or more quality measures of the plant material based on a relation between the measured spectroscopic data and said at least one structural parameter, and generate data indicative of said one or more quality measures of the plant material.

According to some embodiments, the optical inspection unit may comprise at least one optical imaging unit (e.g. RGB camera) and at least one spectrometer unit. The image data may be analyzed to identify region(s) of the plant material sample to which spectrometric measurement(s) (e.g. reflectance spectrometry) is/are to be applied. Alternatively or additionally, the optical inspection unit may comprise a hyperspectral imager unit configured for simultaneously providing the image data and the spectroscopic data of the at least one region of the plant material.

According to some embodiments, the analyzer utility is configured and operable to communicate said data indicative of one or more quality measures of the plant material to a sorting utility. The sorting utility may be associated with a sorting unit configured and operable for transferring the plant material in accordance with said data indicative of said one or more quality measures provided by the analyzer utility.

The system may further comprise a tagging module configured and operable for generating tagging data associating the plant material with the one or more quality measures determined for said plant material, thereby enabling use of said tagging data for sorting said plant material in accordance with said one or more quality measures thereof.

According to some embodiments, the system may further comprise a support assembly comprising a support stage for carrying the plant material within an inspection zone of the optical inspection unit to enable the optical inspection of said at least one region of the plant material. The support assembly may be configured and operable for conveying the plant material to and from said inspection zone.

According to some embodiments, the control unit may comprise a memory utility comprising pre-stored data indicative of predetermined weighting functions, the weighting function describing, for one or more active components in a certain plant material, a relation between spectroscopic data of said certain plant material and one or more structural parameters of said certain plant material.

Alternatively or additionally, the control unit may be configured for accessing a storage device to obtain therefrom pre-stored data indicative of predetermined weighting functions, the weighting function describing, for one or more active components in a certain plant material, a relation between spectroscopic data of said certain plant material and one or more structural parameters of said certain plant material.

The analyzer utility may be configured and operable for utilizing said pre-stored data indicative of the predetermined weighting functions, and determining the relation between the measured spectroscopic data and said at least one structural parameter of the plant material under inspection.

The analyzer utility may comprise: an image processing module configured and operable for receiving and processing the measured image data and determining at least one of said one or more structural parameters of the at least one region of the plant material; a spectrum analyzer configured and operable for receiving and analyzing the measured spectrometric data utilizing said pre-stored data to identify the weighting function corresponding to said at least one structural parameter, and determine corresponding data indicative of the active material content of said plant material; and a quality measure module configured and operable for determining a quality measure of said plant material based on said active material content thereof.

According to some embodiments, the plant material may be cannabis plant material and said at least one region comprises a cannabis flower. The at least one structural parameter may comprise trichomes distribution in said region. The at least one structural parameter may further comprise data about density value of trichomes. The quality measure may comprise data indicative of quantity of said at least one active materials corrected per density of structures.

The quality measure may comprise data about cannabinoids content of said plant material. The data about cannabinoids content may relate to weight percent (% w/w) of said cannabinoids. The cannabinoids may comprise at least one active ingredient selected from the following: CBDA, CBD, CBG, CBN, CBC, □8-THC, □9-THC, TERPENS and THCA.

The present invention also provides a control system for use in determining a quality measure of a plant material. The control system comprises: a data input utility configured to receive measured data comprising measured image data and measured spectrometric data corresponding to of the same at least one region of a plant material; an analyzer utility configured and operable to analyze the measured image data and determine at least one structural parameter of the plant material, utilizes a predetermined relation between spectroscopic data and one or more structural parameters of a plant material, and determine one or more quality measures of the plant material, generate data indicative of said one or more quality measures of the plant material; and a data communication utility configured to transmit output data indicative of said one or more quality measures to a storage device.

According to one other broad aspect of the invention, the present invention provides a method for use in determining a quality measure of a plant material, the method comprising:

providing measured image data and measured spectrometric data of the same at least one region of the plant material, processing said measured image data and determining at least one structural parameter of the plant material in said at least one region thereof, utilizing a predetermined relation between spectroscopic data and one or more structural parameters of a plant material, and analyzing said measured spectrometric and said at least one structural parameter and determining data indicative of content of one or more selected active materials in said at least one region of the plant material, and determining said quality measure in accordance with said data indicative of the content of said one or more selected active materials.

The analyzing step may include determining weighted spectrometric data corresponding to the measured spectrometric data, based on said relation, and using the weighted spectrometric data to determine said data indicative of the content of one or more selected active materials. The relation may be determined from a plant material database comprising data about a plurality of plant materials, comprising, for each plant material its respective spectrometric data, data about one or more structural parameters, and chemical data about actual content of one or more active ingredients.

According to some embodiments, said processing of the measured spectrometric data with said at least one structural parameter may include applying data about predetermined relation function indicative of a correction to content of one or more selected active materials determined by said spectrometric data in view of said at least one structural parameter.

The invention also provides for further update of the plant material data determined as described above by collecting/monitoring user experience data (effect of the plant material being used on the users). The invention thus provides a method for use in analysis of plant material quality, the method comprising:

providing a plant material database for a plurality of plant materials, comprising, for each plant material its respective spectrometric data, data about one or more structural parameters, and data about content of one or more active ingredients;

assigning tagging data to each plant material from a plurality of plant materials intended for users, enabling a user to receive the plant material with the assigned tagging data linking the second plant material to corresponding spectroscopic data and at least one structural parameters of the plant material;

upon receiving user related data comprising data indicative of user experience effects associated with use of one or more of the plant materials, creating a user related database;

analyzing the spectroscopic data and one or more structural parameters for the plant materials in the plant material database using said user related database and determining correlation between the said data about one or more active ingredients and user related effect; and updating said plant material database accordingly.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which:

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
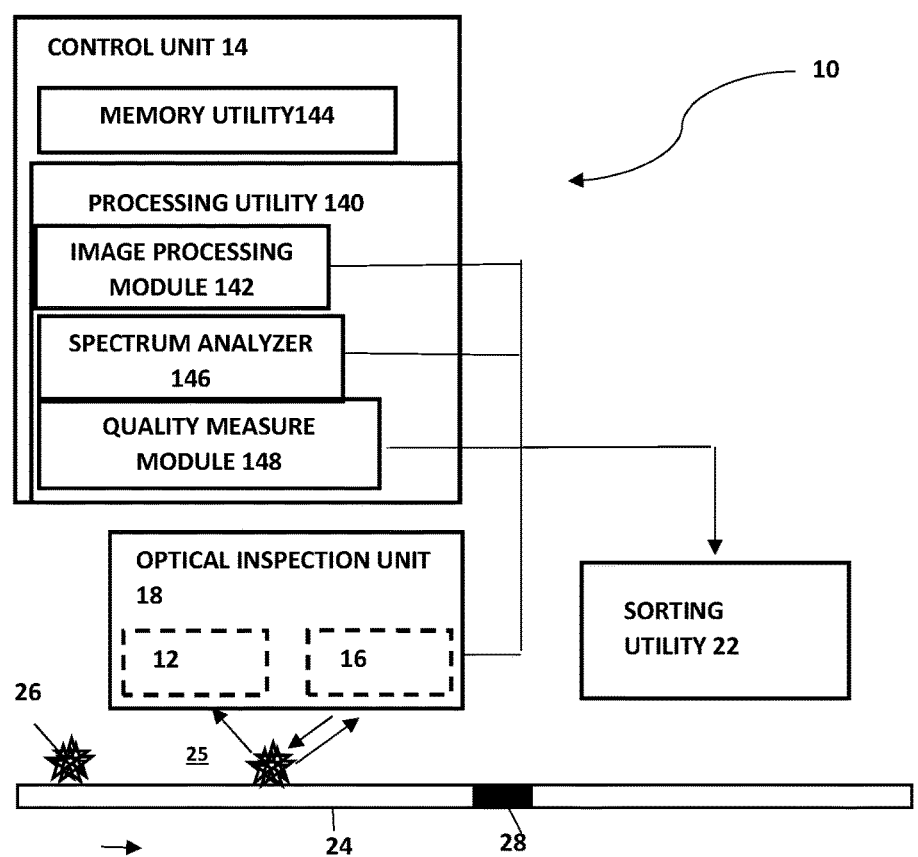
Figure 2:
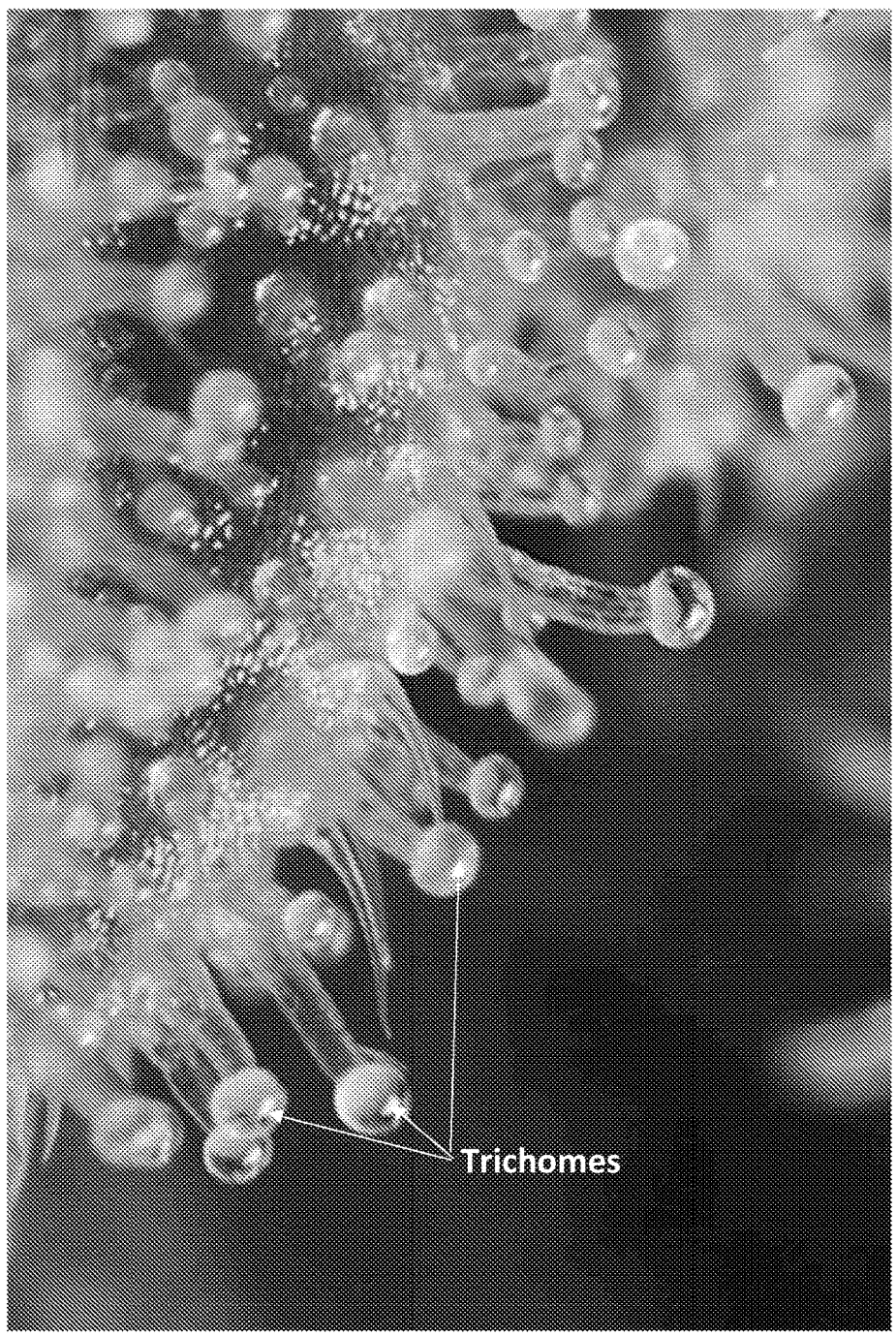
Figure 3:
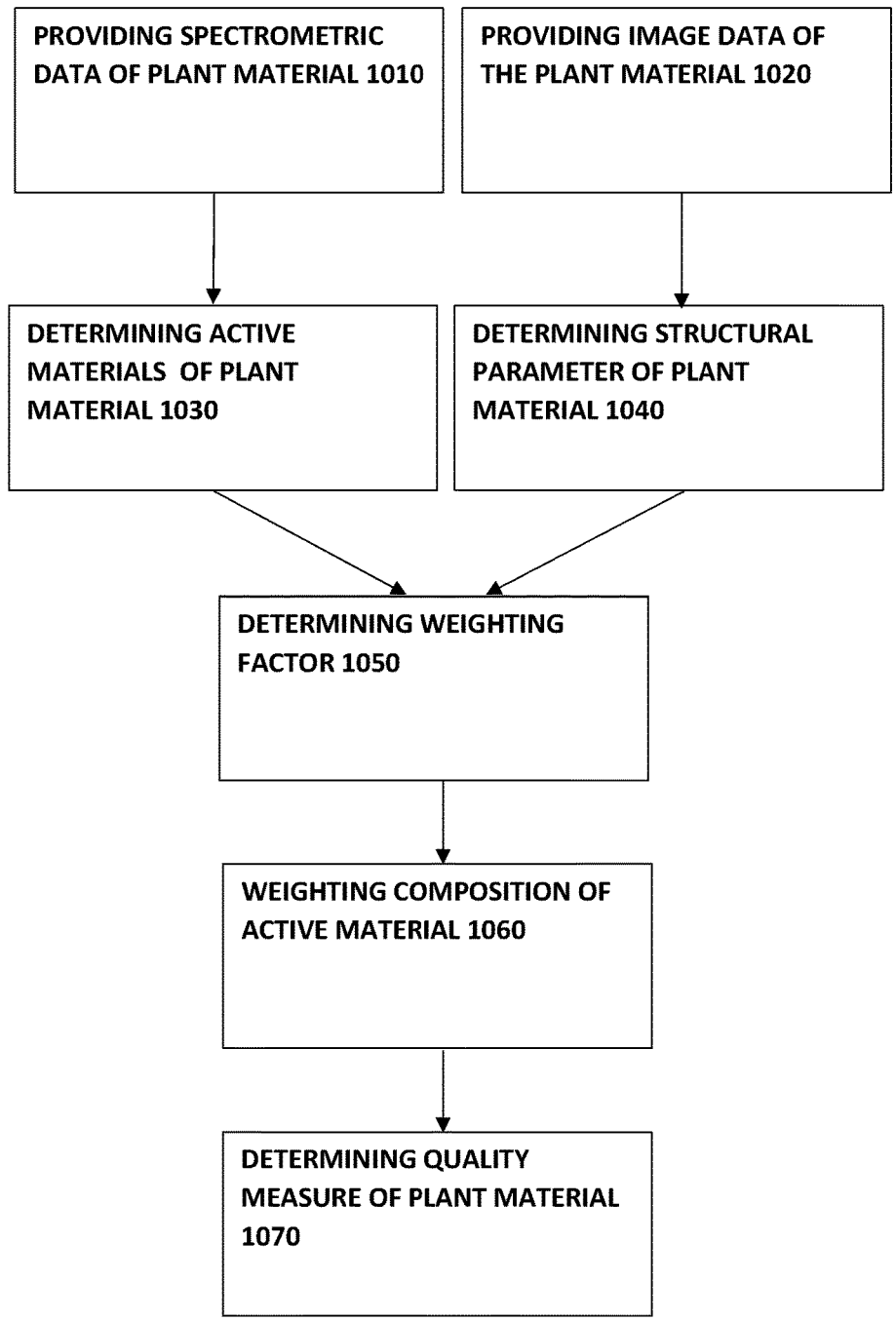
Figure 5:
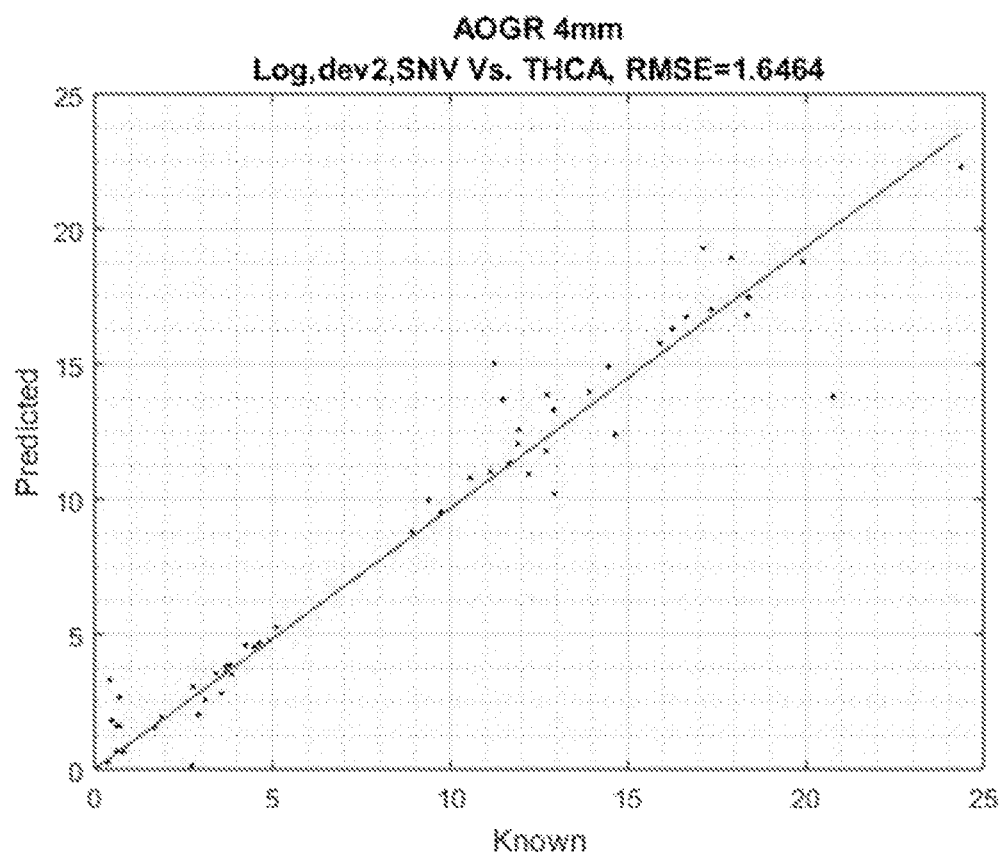
Figure 6:
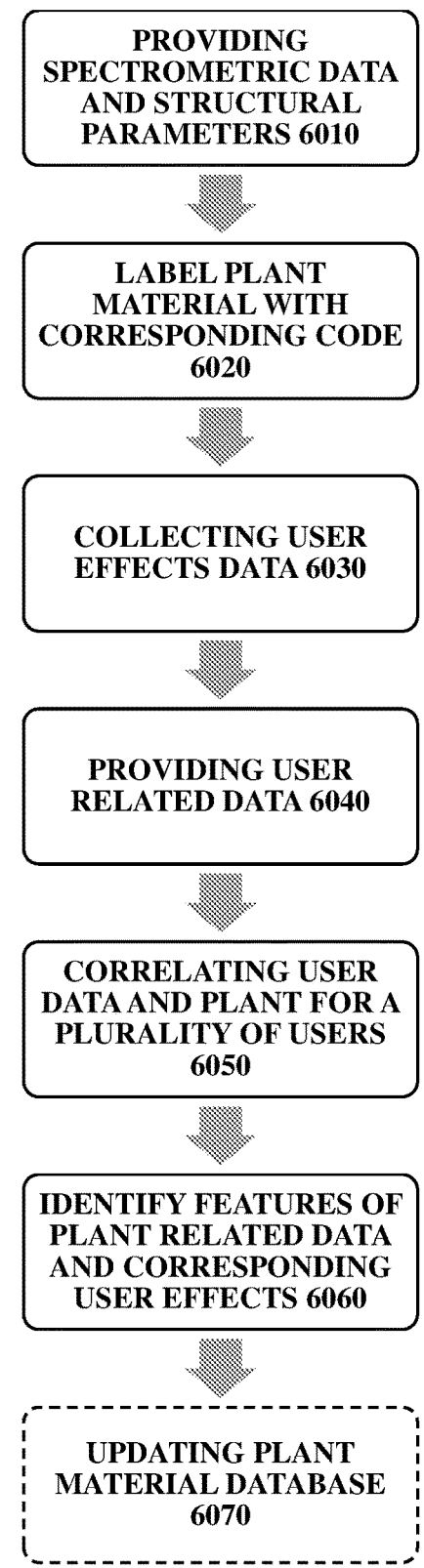
Figure 7:
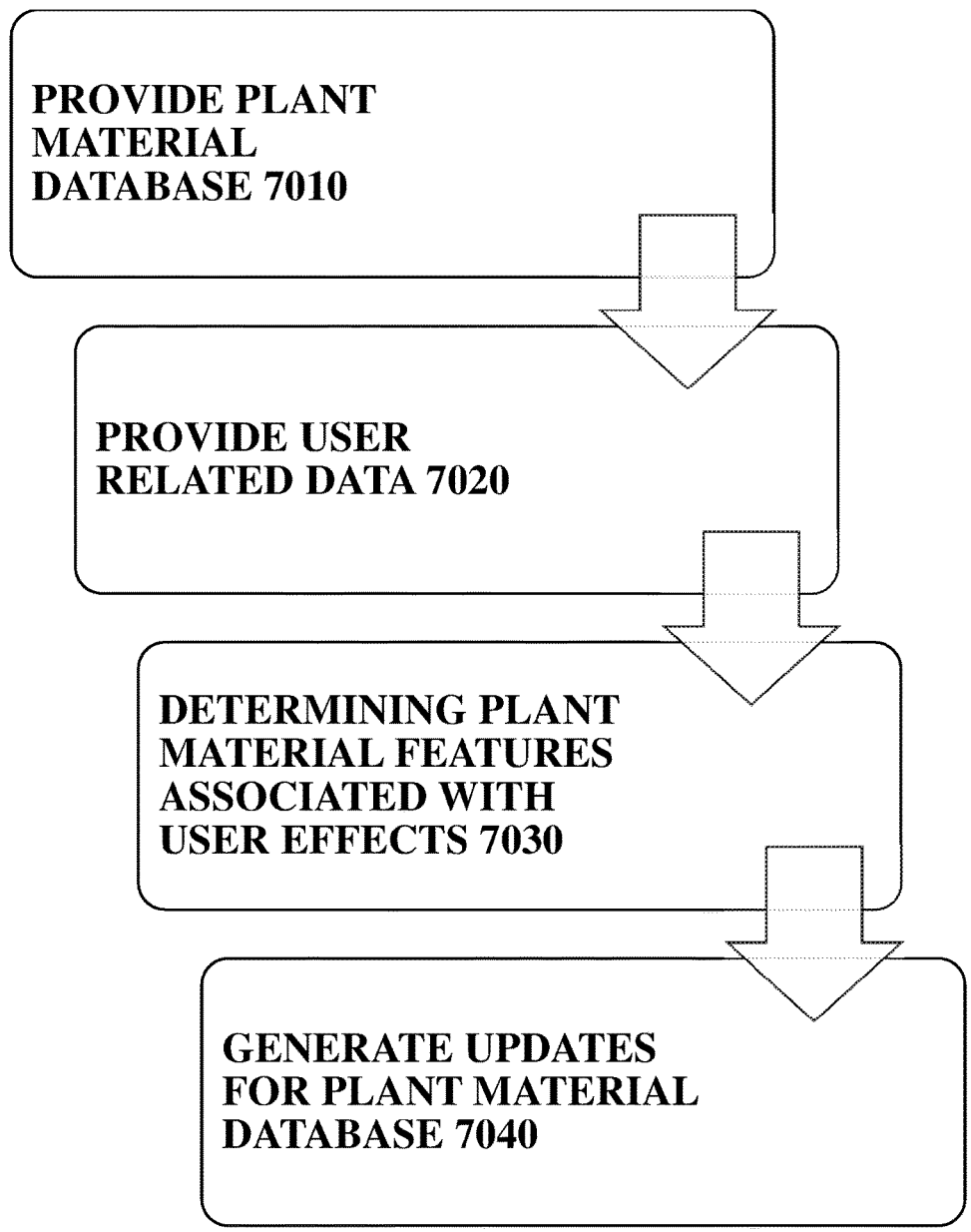
Figure 8:
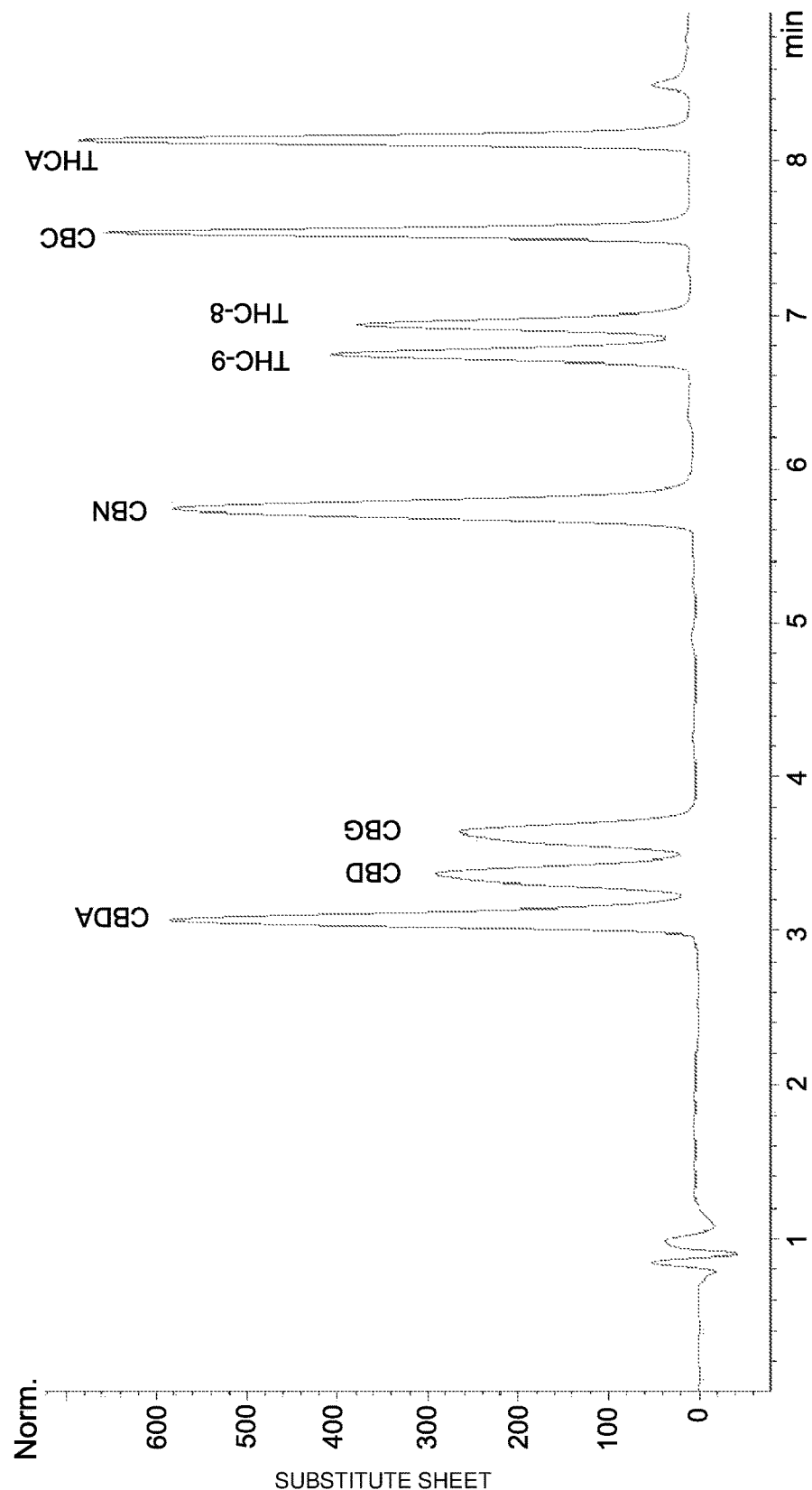
Figure 9:
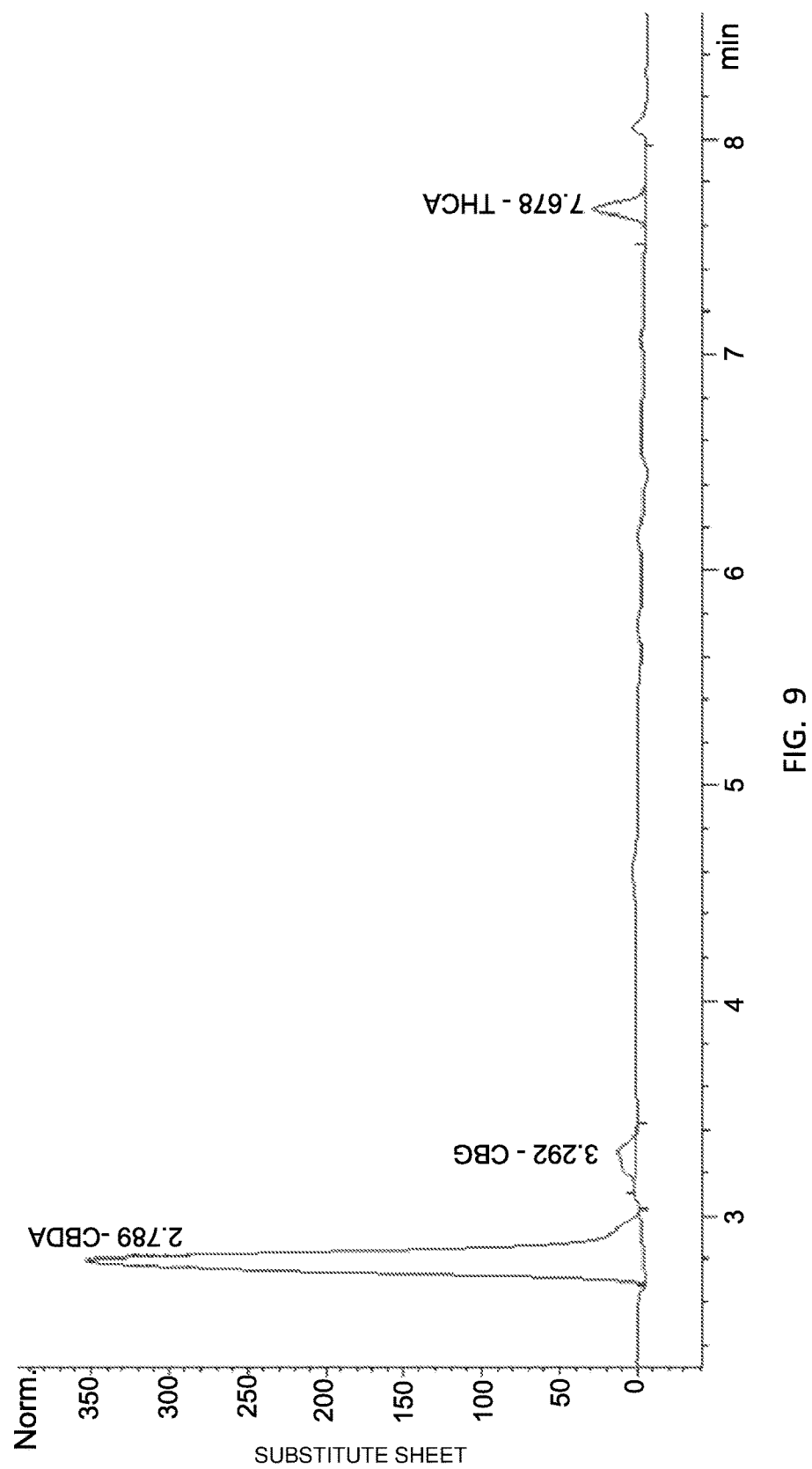
Figure 10:
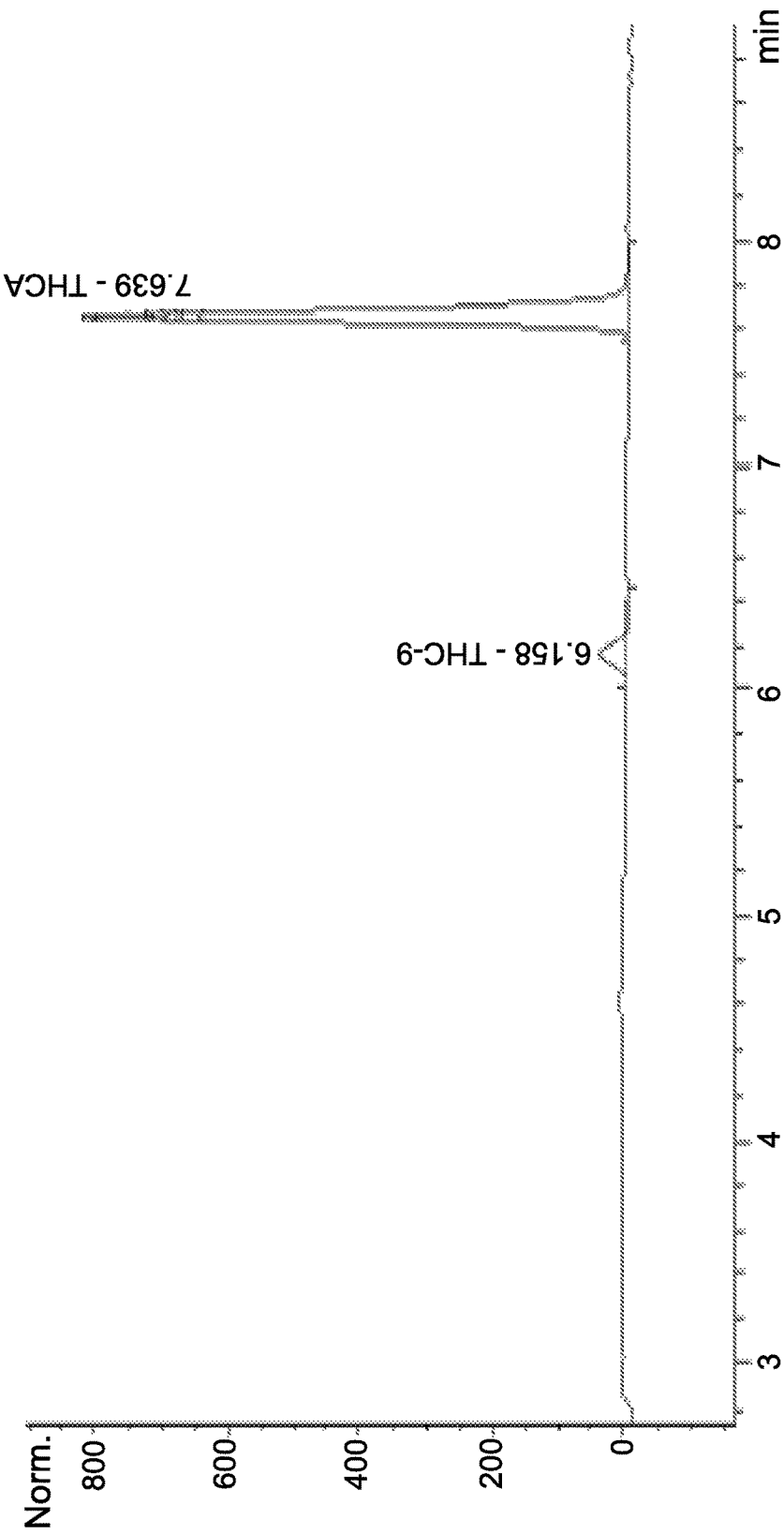
Figure 11:
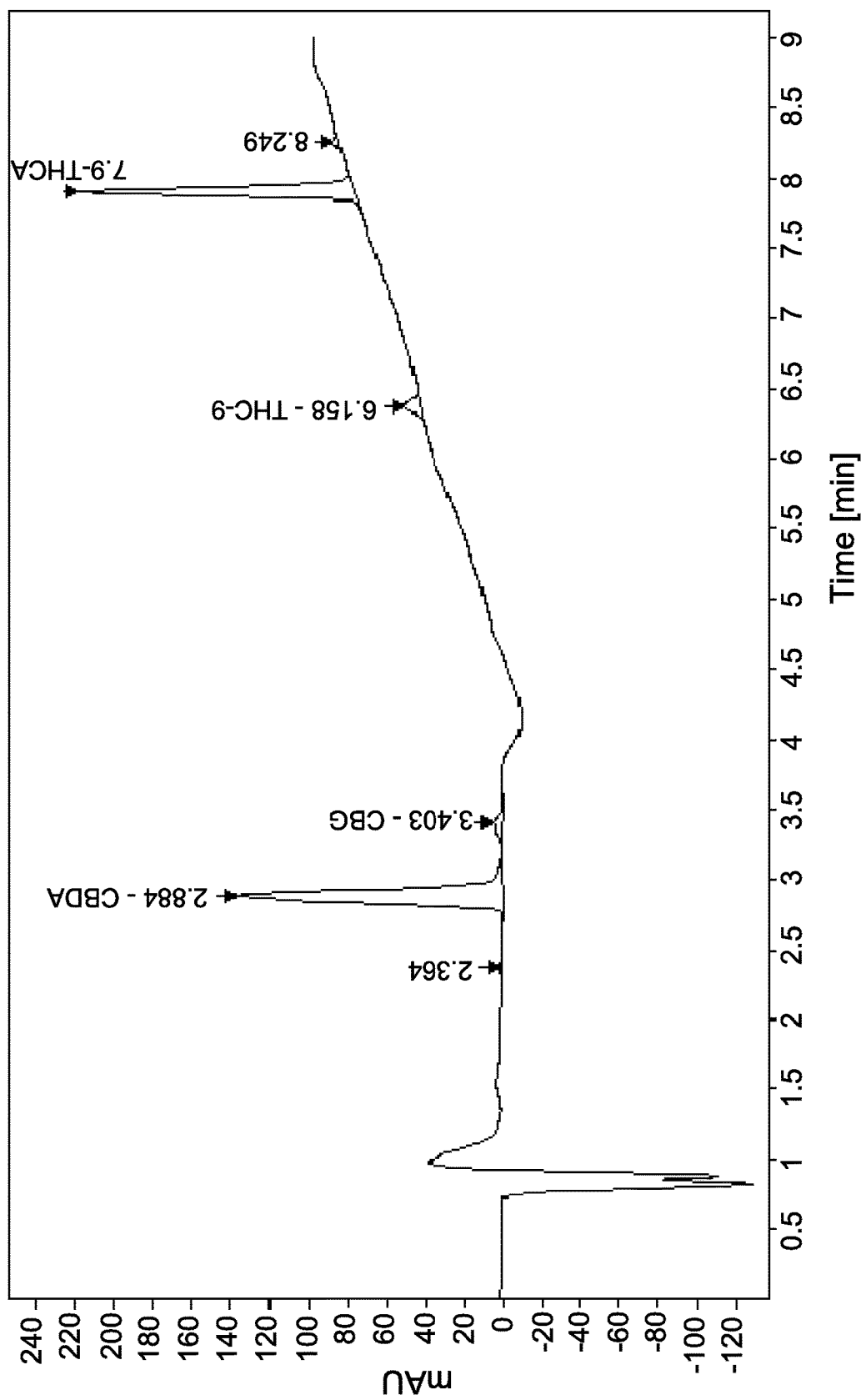
Figure 12:
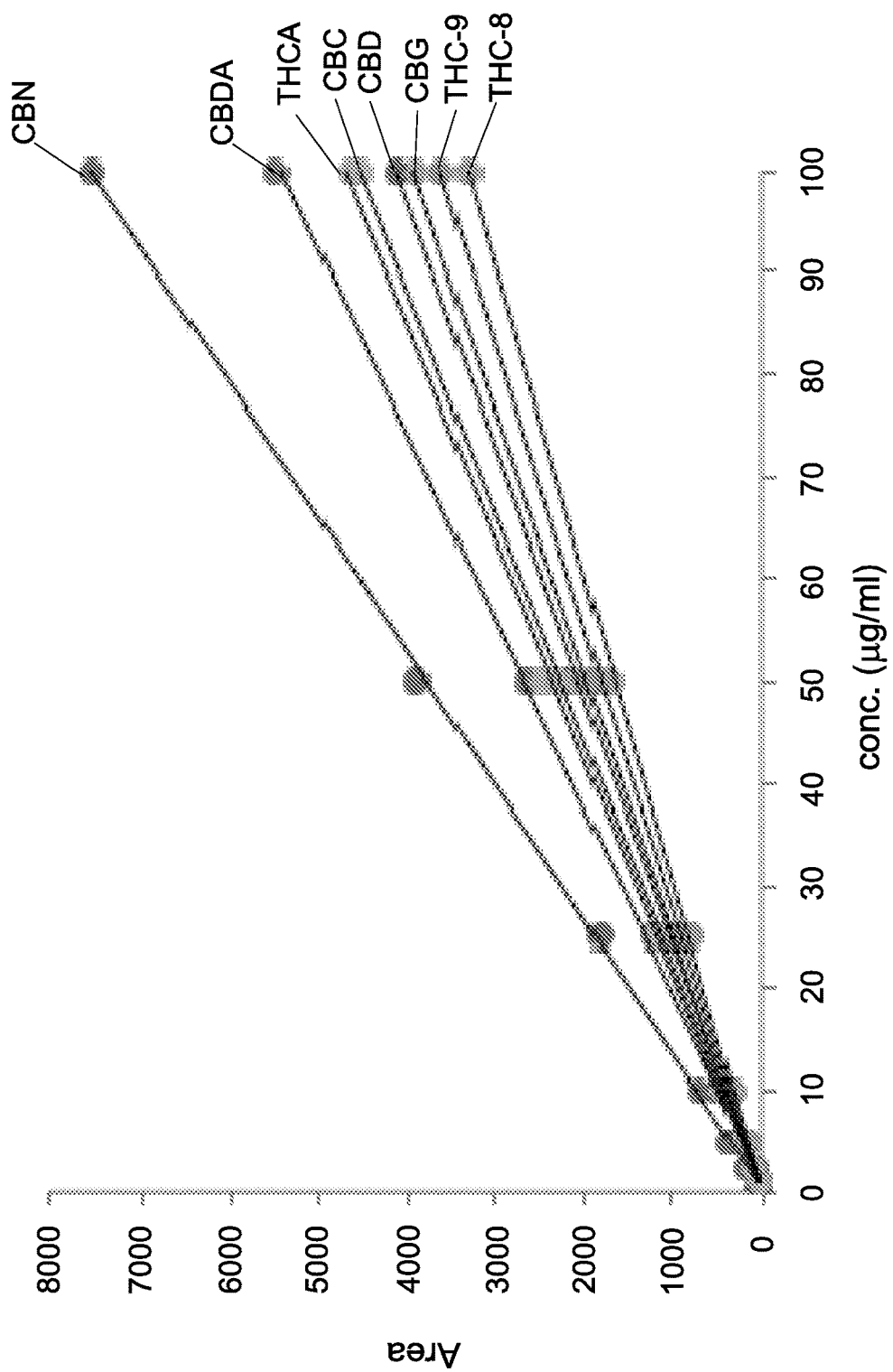
Figure 13:
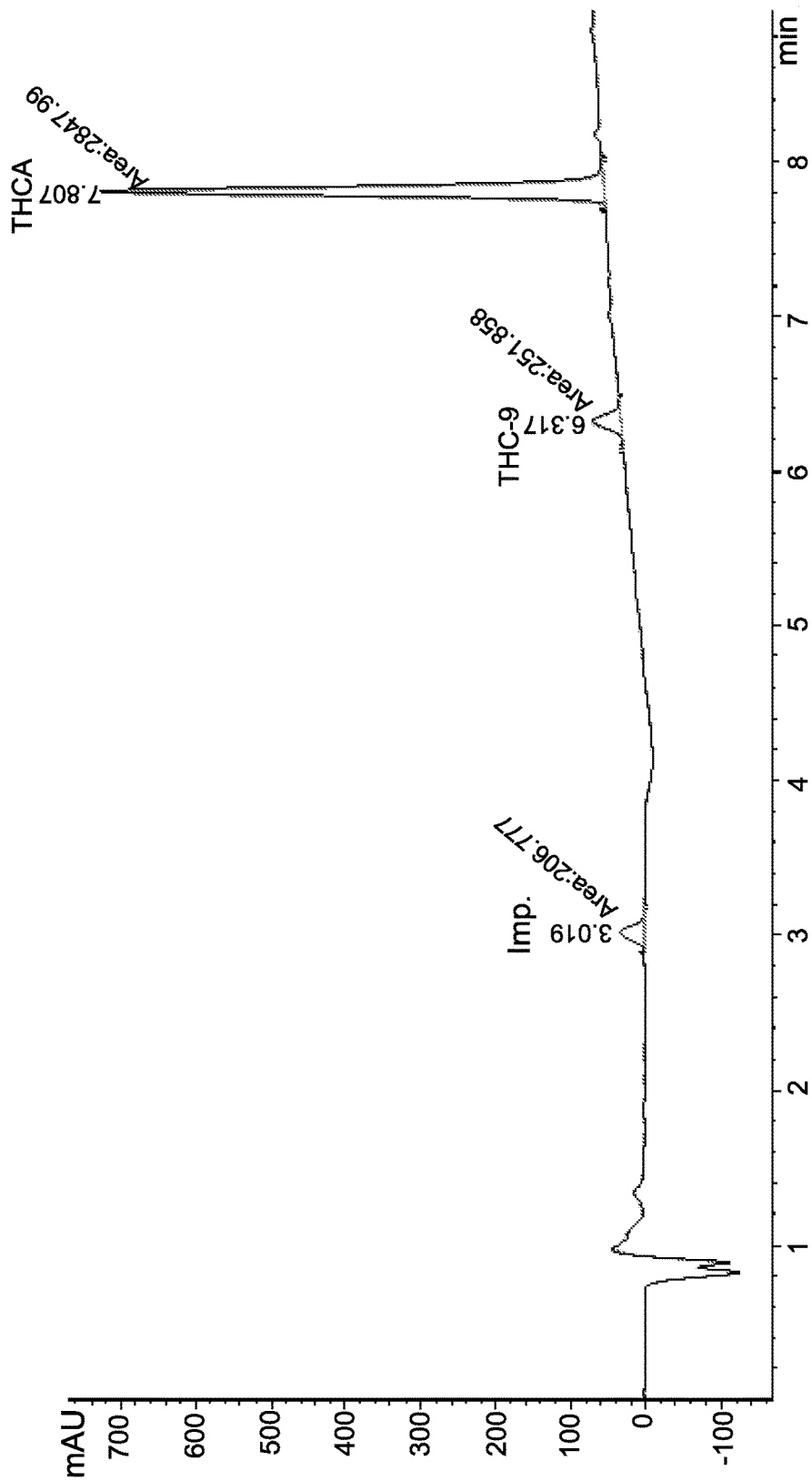
Figure 14:
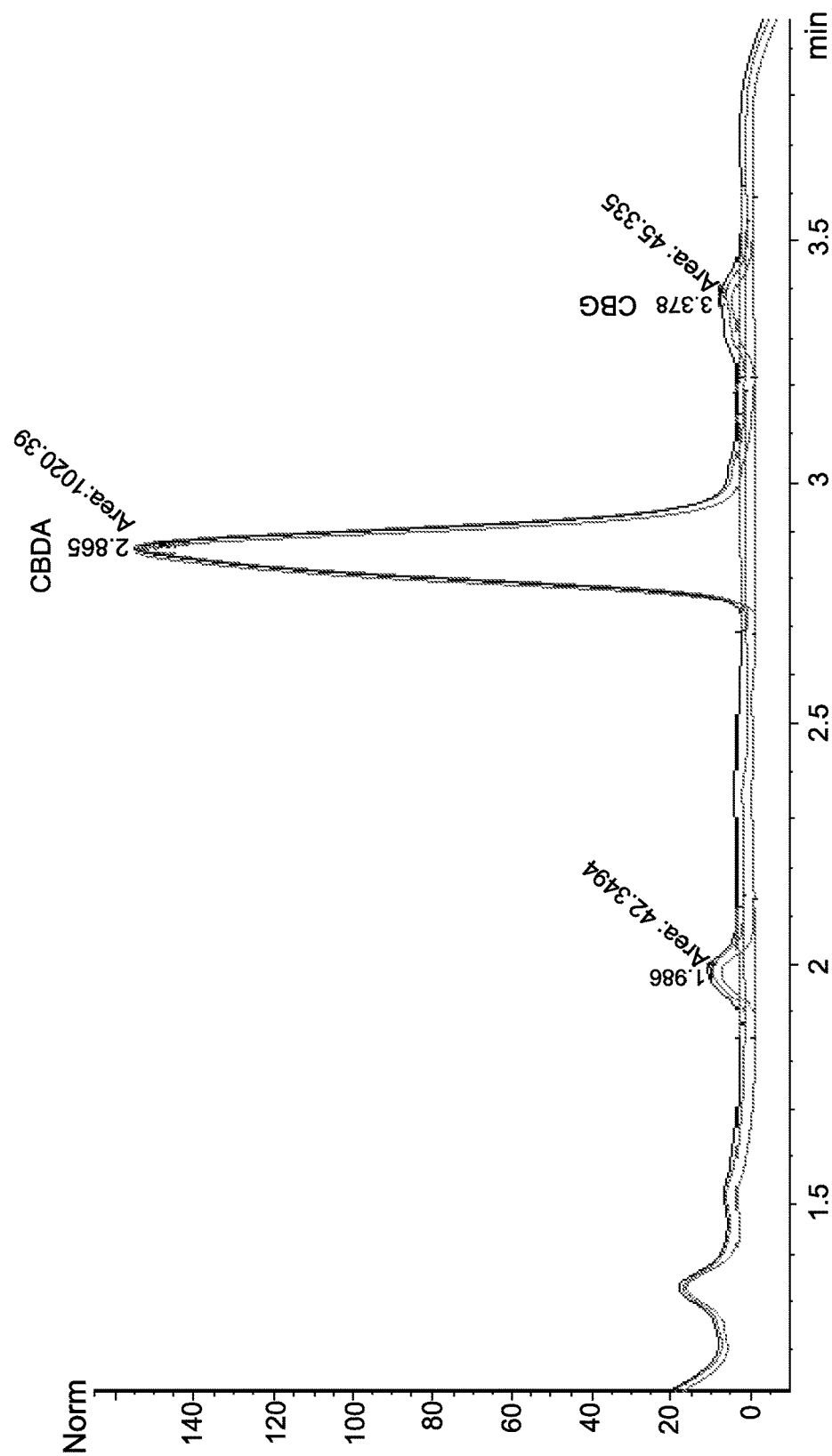
Figure 15:
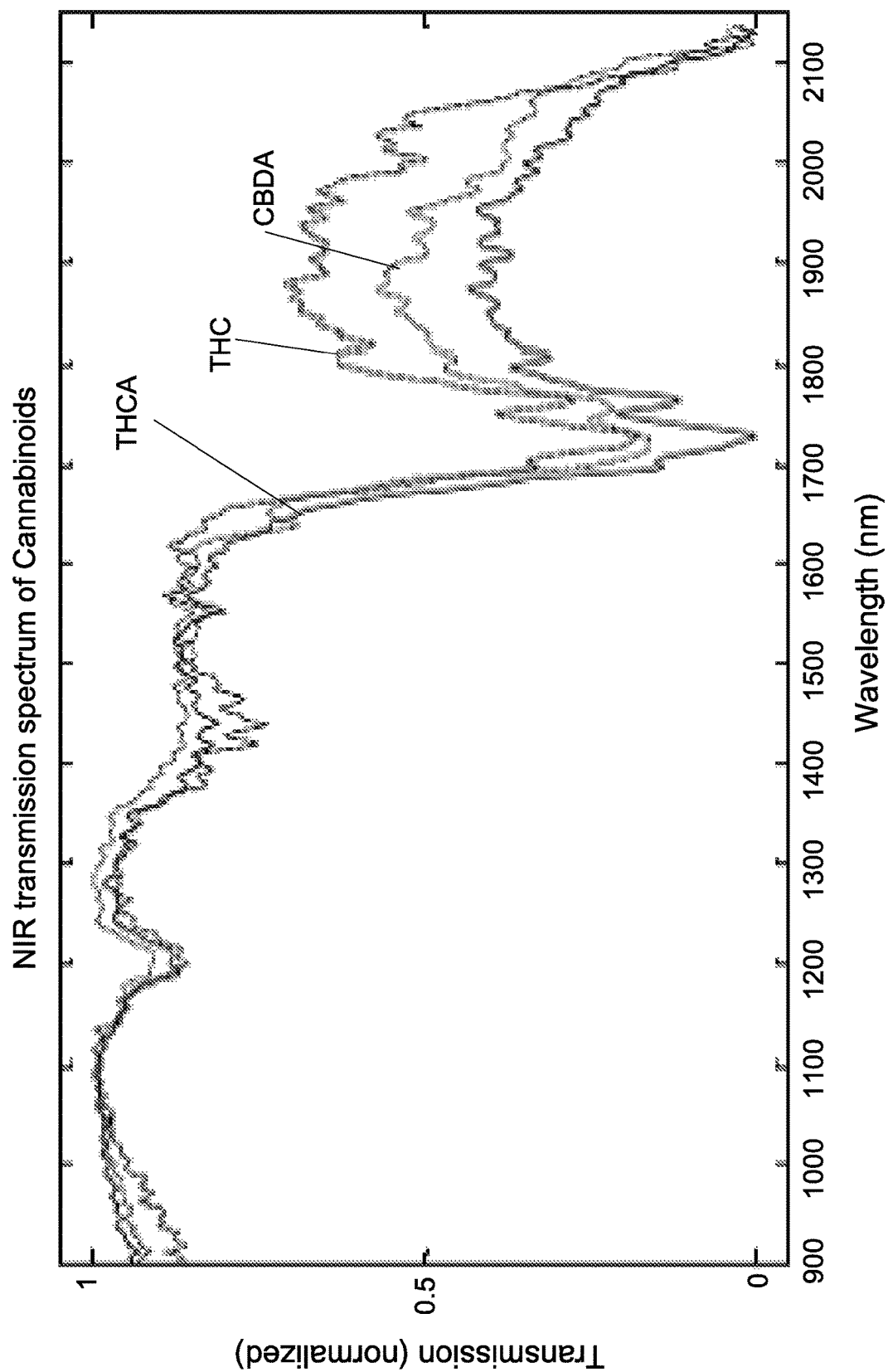
Figure 16:
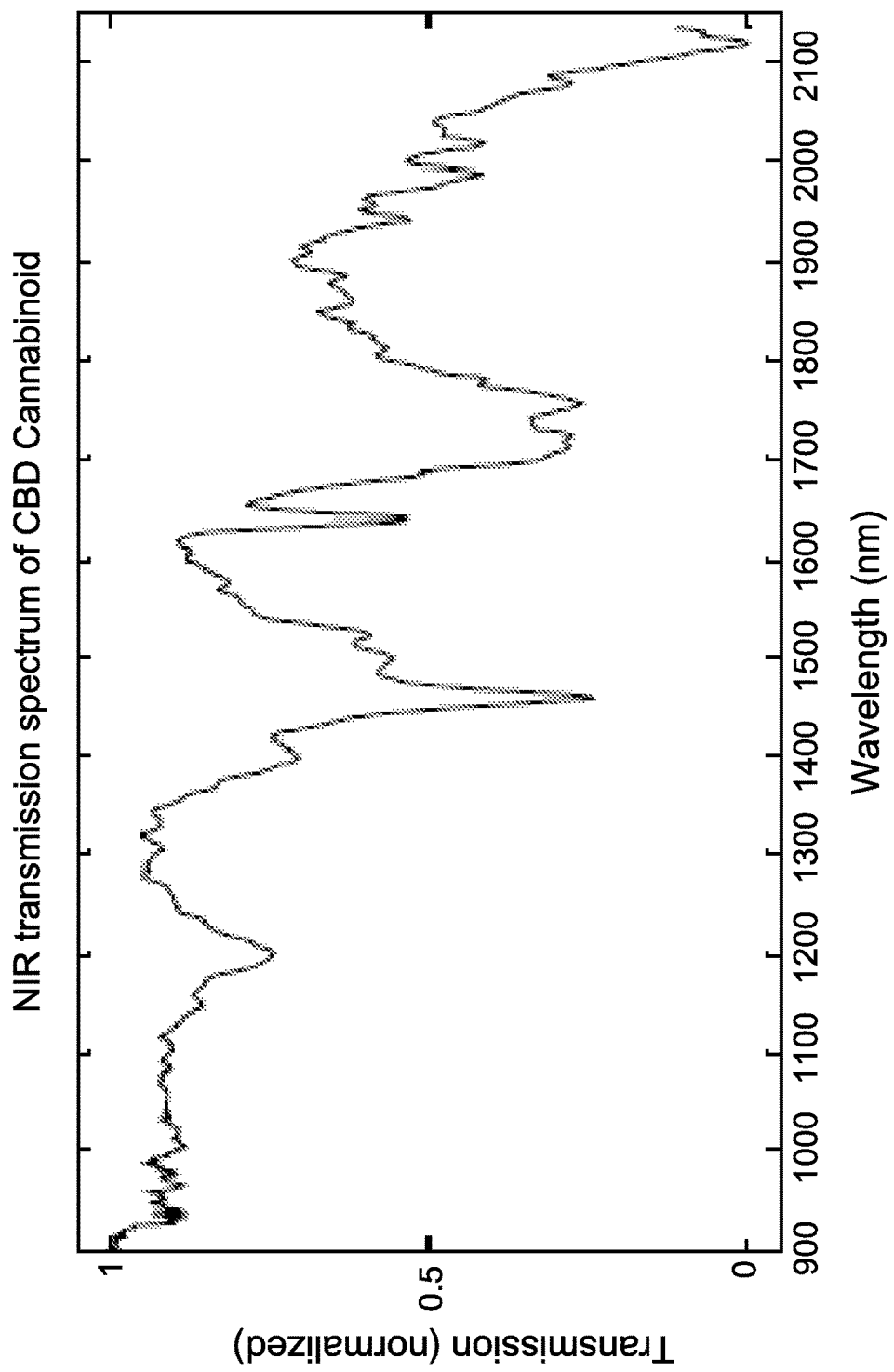

FIG. 1 exemplifies a block diagram of a system of the present invention for determining a quality measure of a plant material;

FIG. 2 is a general art image of trichomes on the surface of a cannabis flower;

FIG. 3 exemplifies a flow diagram of a method for determining the quality measure of a plant material according to some embodiments of the invention;

FIG. 4 exemplifies a flow diagram of a technique of the invention for constructing a database of reference data describing relation between spectral response, structural parameters and material contents of the plant materials, according to some embodiments of the invention;

FIG. 5 shows linear correlation between predicted data and verified material content used in the technique of the invention;

FIG. 6 illustrates a flow chart exemplifying a technique for correlating plant material data with user related data, according to some embodiments of the present invention;

FIG. 7 illustrates a flow chart exemplifying a technique for generating updated plant material database in accordance with collected user related data according to some embodiments of the present invention;

FIG. 8 is calibration chromatogram (50 μm/ml in MeOH) for the various cannabinoids tested;

FIG. 9 is a chromatogram of a CBDA extract from a cannabis sample;

FIG. 10 is a chromatogram of a THCA extract from a cannabis sample;

FIG. 11 is a chromatogram of a CBDA+THCA extract from a cannabis sample;

FIG. 12 is a calibration curve for each of the various cannabinoids tested;

FIG. 13 illustrates stability of a $\Delta^9$-THC and THCA extract over 48 days at $-20°$ C.;

FIG. 14 illustrates stability of a CBDA extract over 48 days at $-20°$ C.;

FIG. 15 illustrates NIR spectral data of THCA, $\Delta^9$-THC and CBDA (brown resin, ~80% purity);

FIG. 16 illustrates NIR spectral data of CBD (white powder, 99% purity); and

Figure 17:
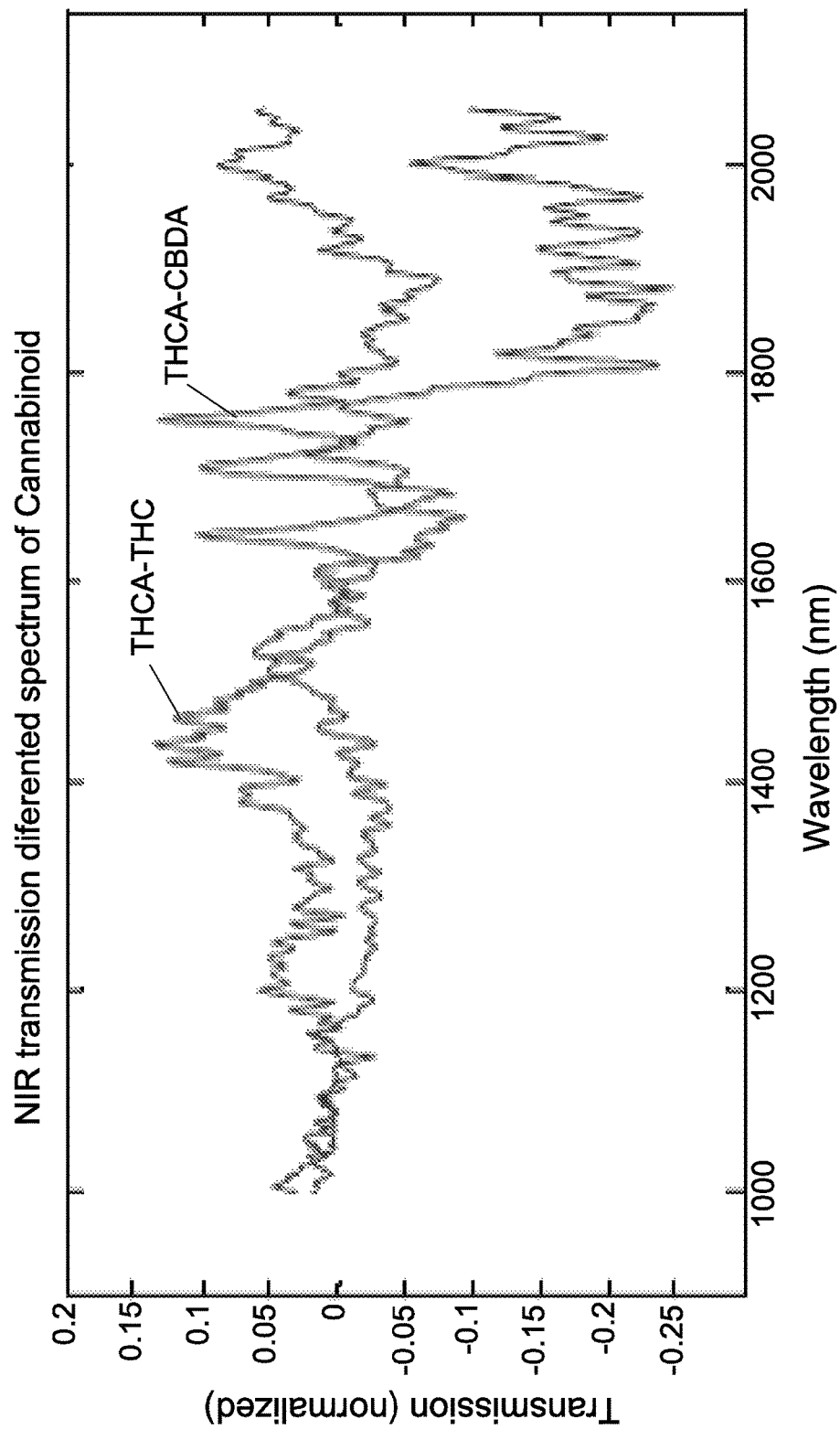

FIG. 17 illustrates a differential spectrum of THCA-$\Delta^9$-THC (brown) and THCA-CBDA (red).

DETAILED DESCRIPTION OF EMBODIMENTS

The present invention provides a system for use in determining plant material quality, and for classifying the plant material according to such quality measure. Typically, the quality of the plant material is determined by concentration, generally measured as weight of selected ingredient per weight % w/w, or content—being the absolute amount in mg of one or more selected active ingredients in the plant material. The present invention can be used for categorizing, and optionally physically sorting, medicinal plants (e.g. cannabis), crop plants as well as ornamental plants. It should be noted that the technique of the invention provides data about plant materials in a non-destructive manner.

In addition, the present invention can also be used for determining data about active materials/ingredients in plants and corresponding effects thereof on users. This may be provided by associating cannabis plants being classified by the technique of the invention with specific objective and/or subjective physiological effects of the plants on patients. The determined effects may thus be associated with specific active materials of the plant as detected while inspecting the plant, thereby allowing large scale collection of data of active materials' effects on users.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. More specifically, the technique of the invention may be applicable for categorizing any plant type having one or more active materials, and certain visible features associated with active materials' production within the plant. The invention is capable of other embodiments or of being practiced or carried out in various ways. Also, it is to be understood that the phraseology and terminology employed herein is for the purpose of description and should not be regarded as limiting. Further, the term active material or active component or active ingredient as used herein interchangeably, should be interpreted broadly as including any chemical of biochemical material that may have any desired activity, known or unknown. Examples of active materials may include various types of cannabinoids, sugars, proteins, caffeine, or any other selected material.

As indicated above, several approaches for quantifying active ingredients of plants are known in the art. Such approaches utilize destructive and time consuming as well as expensive methodologies and equipment (GC and HPLC) or are not sensitive or specific enough for accurate classification of plant material (spectroscopy). This is while, classification of whole plants or excised (and unprocessed) plant material for nutritional or medicinal/recreational use generally requires non-destructive, rapid approaches that can be carried out on a large scale. As such, the above described approaches are not suitable for such purposes.

Thus, the technique of the present invention allows real-time inspection and classification (and optionally physically sorting) of each specific plant material, as well as optional tagging each plant material unit (e.g. each flower, branch etc.) with corresponding data indicative of one or more quality measures. Such tagged data may be provided together with the respective plant material as it arrives to a user, thereby providing data indicative of the specific active material composition in the tagged item.

While reducing the present invention to practice, the present inventors developed an approach which is particularly suitable for classifying whole plant material, or excised plant parts. As is further described herein, the present approach utilizes visible and spectrometric imaging of plant material and may use chemometric correlation of spectrometric information and plant physical characteristics.

Thus, according to one aspect of the present invention there is provided a system for qualifying/classifying a plant material. As used herein, the phrase "plant material" refers to whole plants or excised plant parts in which the qualified tissue is intact (unprocessed). Examples of excised, unprocessed plant material include flowers, seeds, roots, shoots, leaves and the like. A whole plant can be a rooted plant (in a pot or a field) or an uprooted and isolated whole plant.

The system of the invention is configured for inspection of plant material samples/units (e.g. flowers, seeds, fruits, leaves, branches, parts of plant and/or whole plants) and for providing data indicative of one or more quality measures of the plant material samples/units. To this end, the present technique utilizes processing and analyzing of measured data obtained from at least one region of the plant material, where the measured data includes image data (at least one image) and spectral data of the at least one region of the plant material. The image data of a region of the plant material is analyzed for identifying structures of interest (at least one structural parameter of the plant region), and data about these structures of interest in combination with spectral information from the imaged region are used to determine data indicative of one or more quality parameters of the plant region.

As used herein, the term "structures" when made in reference to plants refers to portions of the plant which include the active ingredients of interest. Such structures can be glandular structures (e.g. trichomes), cotyledon, radicle, apex and the like.

Reference is made to FIG. 1 illustrating, by way of a block diagram, a system 10 for inspection and classification of a plant material according to some embodiments of the present invention. The system 10 is exemplified in the figure is formed by an optical inspection unit 18 configured for inspecting at least a region of the plant material 26 located in an inspection zone 25 defined by the field of view of the optical inspection unit 18 and generating measured data, and a control unit 14 configured for signal communication (via wires or wireless signal transmission of any known suitable technique) with a measured data supplier to receive and process and analyze the measured data and determine data about one or more quality measures associated with a unit/sample of plant material being inspected.

It should be noted that the optical inspection unit 18 which is configured according to the invention to obtain measured data enabling classification of a plant material may be a stand-alone device, or may be part of any suitable electronic system. For example, the optical inspection unit 18 may be part of a smartphone device or any other personal communication device.

As will be described more specifically further below, the control unit 14 which is configured (preprogrammed) according to the invention for processing and analyzing the measured data may be part of the optical inspection unit or a stand-alone device/utility, and may receive the measured data directly from the optical inspection unit (on-line operational mode) or from a storage device where the measured data have been previously stored. Such storage device may be a memory of the optical inspection unit or any external storage device, as the case may be. In some embodiments, the control unit may be associated with (e.g. part of or connectable to) a server system receiving and storing the measured data provided by the optical inspection unit via a communication network. In some other embodiments, the software/hardware modules of the control unit are distributed between the optical inspection unit and an external device.

As illustrated in the specific but not limiting example of FIG. 1, the system 10 may be configured and operable for automatic inspection and sorting (e.g. at least providing classification data to be used for further sorting) of a plant material 26 while progressing on a production line. Typically, a support assembly, generally 24, is provided for supporting the plant material being inspected within the inspection zone 25 defined by the optical inspection unit 18 (i.e. to be in the field of view of the optical inspection unit). For example, the support assembly 24 may include a support stage located in the inspection zone, and may also be configured for conveying the plant material 26 to and through the inspection zone. Also, the support assembly may include a weighting unit 28 configured for determining weight of each plant material unit.

As further exemplified in the figure, a sorting utility 22 may be provided. The sorting utility 22 may be associated with a stand-alone device or may be part of the control unit 14 and may serve for storing sorting data with respect to the plant material based on the quality measure(s) thereof. In some embodiments, the sorting utility 22 may be associated with a physical sorting unit/station, e.g. located downstream of the optical inspection unit 18, as the case may be, and configured for sorting/transferring (and possibly also physically tagging/labeling the plant material units) in accordance with data about one or more quality measures provided by the control unit 14, as will be described below.

The optical inspection unit 18 is configured and operable for applying optical inspection to at least one region of the plant material 26 and generating measured data including measured image data and measured spectroscopic data of the same at least one region of the plant material. To this end, the optical inspection unit 18 may include a hyperspectral imager configured for providing both the image data and the spectral data of a region of interest (containing plant material in this case). Alternatively, as shown in this non-limiting example of FIG. 1, the optical inspection unit 18 may include at least one imager (camera unit) 12 configured to acquire image(s) of at least the region of the plant material and generate corresponding measured image data, and a spectrometer unit 16 (e.g. Raman spectrometer) configured for detecting spectral response (in a predetermined wavelength range) of said at least region of the plant material and generate corresponding measured spectrometric data. The measured data (image data and spectral response) are then processed and analyzed by the control unit 14.

As indicated above, the processing and analyzing of the measured data may be performed in real time (a so-called "on-line" mode), or alternatively the measured data may be collected off-line and properly stored to be processed later on Similarly, the physical sorting of the plant material if needed, being based on the inspection data, may be performed "on-line", i.e. immediately after the inspection; or later on at a remote sorting station based on the previously stored inspection data. The inspection data includes one or more quality measures of the plant material, preferably together with tagging data associating the quality measure(s) with the respective plant material.

The imager (camera unit) 12 may be of any suitable configuration for acquiring one or more images of the plant material being inspected using visible light and/or infra-red. The camera unit 12 may be colour camera (RGB), greyscale camera, an infra-red camera, a hyperspectral camera or any combination of these cameras for imaging the region of the plant. The camera unit 12 is configured for transmitting image data directly to the control unit 14 (on-line mode) or to a storage device (off line mode), as the case may be, for data processing and analysis. Generally, the captured image data can be used directly (as is) for analysis, or in some embodiments, the control unit 14 may apply initial pre-processing to enhance contrast, sharpen edges or the like. As indicated above, the processing of the measured data may be distributed between modules integral with the optical inspection unit, and modules at a remote device (e.g. remote server utility). For example, some initial pre-processing of the measured data is carried out at the optical inspection unit (or electronic device carrying such optical inspection unit) and the pre-processed data is formatted for transmission to the external device.

According to some embodiments, the spectrometer unit 16 is configured to operate in a spectral range selected according to the plant material being inspected and structures being interrogated/inspected, as well as in accordance with one or more active materials of the plant to be identified. For example, in the case of cannabis plant material, where the active materials associated with quality measures may be various cannabinoids, the spectrophotometer unit 16 may typically be configured with a Near Infra-Red (NIR) wavelength range of 900-2100 nm which is suitable for interrogation of the trichomes of the specific plant material (e.g. flowers). In this connection, reference is made to FIG. 2 showing a cannabis flower (constituting a sample/unit of plant material) and trichomes spread on the flower region.

Near infra-red (NIR) spectrometry is generally known in the art and can be used to detect and quantify cannabinoids in whole plants or plant material. Generally, NIR spectrometers/cameras are configured for collecting and analyzing the absorbance/reflectance spectrum (generally referred to as spectral response) of samples irradiated with light at wavelengths between 700 nm and 2500 nm. NIR radiation is highly penetrative and thus can be applied to the sample without any preparation. Although the resulting absorbance or reflectance spectra is not highly discriminative it can be used to quantify active ingredients by using NIR calibration models. For example, quantitative information of organic components of plant material can be derived from NIR spectral data by using validated quantitative data obtained via HPLC or another quantitative approach.

It should be noted that the NIR spectrometer unit 16 may generally include a light source, a detector, and a dispersive element (such as a prism, or, more commonly, a diffraction grating) to allow the intensity at different wavelengths to be recorded. Fourier transform NIR instruments using an interferometer are also common, especially for wavelengths above ~1000 nm. Depending on the sample, the spectrum can be measured in either reflection or transmission mode or both of such modes. It should also be noted that the spectrometer can utilize an external light source, as the case may be. The light source may be configured as a common incandescent or quartz halogen light bulbs providing broadband illumination including near-infrared radiation, and may be used for analytical applications. Light-emitting diodes (LEDs) may also be used and offer greater service life and spectral stability as well as reduced power requirements. A laser source can also be used for NIR imaging as it has the potential to reduce signal to noise ratio once specific adsorption bands are correlated with an active ingredient of interest.

The type of detector used in the spectrometer unit 16 may depend primarily on the range of wavelengths measured. Silicon-based CCDs are suitable for the shorter end of the NIR range, but are not sufficiently sensitive over most of the range (over 1000 nm). InGaAs and PbS devices are more suitable though less sensitive than CCDs. In certain diode array (DA) NIRS instruments, both silicon-based and InGaAs detectors are employed in the same instrument. Such instruments can record both UV-visible and NIR spectra 'simultaneously'. Instruments intended for chemical imaging in the NIR may use a 2D array detector with an acousto-optic tunable filter. Multiple images may be recorded sequentially at different narrow wavelength bands.

Additionally or alternatively to NIR spectrometer described above, the spectrometer unit 16 may be configured as, or include, a Raman spectrometer unit. Generally, the principles of Raman spectroscopy and the configuration and operation of Raman spectrometer are well known in the art and therefore need not be described in details, except for noting the following: Raman spectrometers utilize inelastic scattering of light, typically laser illumination, interacting with matter where the scattered light shows a shift in energy (wavelength) providing information about vibrational modes of the inspected material. Generally, the use of Raman spectroscopy may be advantageous over NIR spectroscopy as water molecules have negligible trace in Raman spectrum. This allows obtaining spectrometric data from wet, or moist, plant material without the need for drying prior to inspection.

As indicated above, the optical inspection unit 18 may be configured to include hyper spectral imager in place of visible camera 12 and NIR spectrometer/imager 16. Generally, hyperspectral imaging, like other spectral imaging, collects and processes information from across the electromagnetic spectrum. Hyperspectral imaging obtains a spectrum for each pixel in the image of a scene, and can be used to identify objects, ingredients or processes.

The optical inspection unit 18, utilizing a hyperspectral imager, or including imaging and spectrometer units 12 and 16, is configured and operable to provide measured image data and measured spectrometric data from the same region(s) of the plant material. As indicated above, this data is transmitted (using any known suitable data/signal transmission) to the control unit 14, or to a storage device to which the control unit 14 has access.

The control unit 14 is typically a computer device including data input and output utilities which are not specifically shown, memory utility 144, and an analyzer (processor) utility 140. The latter is configured for processing and analyzing the measured image data and measured spectral response data of the inspected plant material to determine one or more quality measures of the plant material. To this end, the processor 140 is configured (preprogrammed) to analyze the measured image data and determine structural parameter(s) of the plant material in the region thereof being inspected, and analyze the measured spectroscopic data and determine a relation between the measured spectroscopic data and the structural parameter(s). This relation is then further analyzed (using pre-stored reference data, as will be described further below) to determine one or more quality measures of the plant material. The control unit generates respective output data indicative of the quality measure(s) of the plant material. This data may be used for appropriately sorting/classifying the plant material.

More specifically, as exemplified in FIG. 1, the analyzer/processor utility 140 of the control unit 14 includes an image processing module/utility 142 configured and operable for processing the received image data for automatically detecting presence and location of one or more regions of interest, i.e. selected specific structures (e.g. trichomes) in the image, and for determining one or more structural parameters of the plant material in the region of interest. Such structural parameter(s) may include number or density of the selected specific structures (where applicable).

The control unit 14 utilizes the data about number of selected structure, typically together with pre-provided parameters of the camera unit 12 and inspected region of the plant, for determining structure density information for the selected structures and inspected plant. The parameters of the camera unit 12 and the inspected region typically include size of the inspected region and field of view of the camera unit. The parameters of the camera unit may be previously provided and stored in a memory utility 144 of the control unit 14. Such camera unit parameters and inspected region parameters (image field size) are typically selected according to the plant material being imaged and the structures of interest. The area of the image field can be percentage of imaged frame (in % of frame). The spectrophotometer unit 16 (may also be configured as or referred to as spectral imager) is configured for obtaining spectral information from the region of the plant material being inspected. Generally the spectrometer unit 16 is configured for collecting spectrometric data from a region that is similar to the imaged frame. The spectrometric data or spectral response (absorption, reflection and/or transmission), e.g. NIR and/or Raman spectrum, of the region of the plant material includes information about active materials in said region.

As indicated above, the image data and the spectrometric (e.g. NIR and/or Raman spectrum) data are processed and analyzed by the control unit 14. To this end, the control unit 14 includes the processing utility 140 configured and operable for carrying out various types of data processing and image processing utilizing one or more software and/or hardware modules. Specifically, the processing utility 140 may utilize various known software modules for carrying out for example: Principle Component Analysis (PCA), Python Hyperspectral Toolbox. Gerbil a hyperspectral visualization and analysis framework. https://en.wikipedia.org/wiki/Hyperspectral_imaging—cite_note-38Erdas Imagine, a remote sensing application for geospatial applications, ENVI a remote sensing application, FECOM Object Learning Software (OLS), industrial in-line hyperspectral feature processing, MIA Toolbox for multivariate image analysis, MicroMSI a remote sensing application, A Matlab Hyperspectral Toolbox. Other Hyperspectral tools in MATLAB. MountainsMap HyperSpectral—cite_note-42 a version of MountainsMap dedicated to the analysis of hyperspectral data in microscopy, Opticks a remote sensing application, Perception System; in-line hyperspectral imaging for industry, Scyllarus, hyperspectral imaging C++ API, MATLAB Toolbox and visualizer.

Generally, as indicated above, the control unit 14 (its processing utility 140) is configured for receiving the visible (image data) and spectral (spectrometric) data obtained by the optical inspection unit 18, and processing the image data to determine data about density of selected structures (generally, determine one or more structural parameters), associated with production of selected active material, within the plant material (e.g. structure units per/$mm^2$), and processing the spectroscopic data to determine data about a quantity of one or more selected active ingredients in the region of the plant material interrogated.

It should be noted that as the inspected region of the plant material generally includes areas covered by the selected structures of interest (e.g. trichomes), as well as additional plant elements devoid of the selected structures, the spectral signal (spectrometric data) obtained from the inspected region of plant material generally reflects such heterogeneity of plant tissue. Thus, the spectrometric data may typically be composed of multiple signal components, possibly overlapping, indicative of absorbance/reflectance wavelengths (or wavelength bands) with various peak heights (intensity). Such signals, although include data about quantity of the selected active material/ingredients(s), include high noise level associated with spectrometric data originated by additional materials present in the region of the plant and are thus suboptimal.

To this end, the processing utility 140 operates for correlating data about density of the selected structures in the inspected region of the plant material with spectrometric data obtained from the same region to accurately determine data about quantity of one or more selected active materials/ingredients of the plant material. As is described in the Examples section further below, the present technique enables quantitative detection of selected active materials based on spectroscopic data correlated with the image data from the plant material while in its unprocessed phase. This enables determining quality measure(s) of the plant material while not requiring processing (grinding) of plant material to increase the accuracy of NIR spectroscopy by increasing homogeneity of the plant material. The technique of the present invention acknowledges the fact that production of selected active materials in the plant material is not necessarily homogeneous, for example, trichomes, and the cannabinoid-containing structures on the flower surface of cannabis, do not cover the entire surface of the flower. Thus spectroscopic data of the unground material is more heterogenic and spectroscopic data (e.g. NIR spectrum reading) thereof is to be weighted and/or corrected for homogeneity by a factor associated with the density of the trichomes. This is exemplified in FIG. 2 showing a picture of a region of cannabis flower and trichomes spread on the flower region.

Referring back to FIG. 1, the control unit 14 includes the processing utility 140 including software and/or hardware modules for performing certain processing tasks. According to some embodiments, the processing utility 140 may include image processing module 142, spectrum analyzer 146 and quality measure module 148.

The image processing module 142 is configured and operable for receiving the image data (from the optical inspection unit 18 or a storage device, e.g. internal memory of the control unit or a separate storage device) and for processing the received image data to determine one or more structural parameters, e.g. data about quantity and density of selected structures (e.g. trichomes) of the plant material, associated with storing and/or producing one or more selected active materials. The image processing module 142 may also determine data about additional parameters of the selected structure such as size statistics (e.g. average and standard deviation of size), color distribution of the structures, etc. The output of the image processing module 142 including the determined data about the structure density is utilized by the spectrum analyzer 146. The spectrum analyzer 146 is configured and operable for receiving spectrometric data (from the optical inspection unit 18 or a storage device, e.g. internal memory of the control unit or a separate storage device), and utilizing the spectrometric data and the structure density for determining existence and quantity of one or more selected active materials. The spectrum analyzer 146 utilizes data about the structure density in correlation with the spectrometric data for adjusting the spectrometric response in accordance with the density of the relevant structures of the plant for determining corrected data about composition and quantity of active material(s) of interest in the plant material.

Thus, the spectrum analyzer 146 is configured and operable for correcting the determined data about quantity of active material as obtained from the spectral data utilizing data about structure density and correlating it with spectral information. This will be described more specifically further below.

The quality measure module 148 utilizes data about quantity and identity of the active materials determined by the spectrum analyzer 146 for determining one or more quality measures of the plant material. To this end, the quality measure module 148 may utilize additional data pieces, such as data about number of relevant structures, color of the plant material, as well as data about weight of the inspected plant material, for determining corrected quantitative information providing quality value for the plant material.

The correlation between the spectrometric data and the density of relevant structure determined according to the image data may be first order correlation or correlation of higher order. Additionally, such correlation may be linear or semi-linear in accordance with the determined density and/or with data about spectral response of the selected active material that is preferably pre-stored (e.g. in the memory utility 144 of the control unit 14).

For example the quantity of active ingredient(s) obtained from the spectral data can be corrected for the density of the structures using a linear or semi-linear relationship: the denser the structures, the lower the correction weight applied to the measurement provided by the spectrometric data. For example, the NIR spectral peak(s) value, or the quantity value derived from the NIR spectral peak(s), of a region having a structure density of 25% (25% of the regions is covered by the structures) can be multiplied by a factor of 4 to provide corrected quantity. Accordingly, if the image data indicates 50% coverage, the correction to the values determined by the spectrometric data may lead to a correction by a factor of 2. Specifically, the corrections are generally further corrected such that for 25% coverage the correction factor may be of 3-5, and for 50% coverage the correction factor may be of 1.5-2.5. Typically, greater coverage can also result in more spectral artifacts or noise, which is compensated by proper selection of the correction factor.

More specifically, according to some embodiments, calibration data may be provided and stored in the memory utility 144 of the control unit 14. The calibration data is indicative of a correction function, $f_j^s(d)$, indicating a value of correction factor f for active material j in accordance with spectrometric value s and structure density d as determined from the image data. Such calibration data may be prepared and stored as reference data being determined using reference samples and comparing data acquired by the technique of the invention with HPLC analysis of the samples, to provide data about actual composition and quantities of the selected active materials.

In this connection, reference is made to FIG. 3 exemplifying a flow diagram of general operations of the technique of the present invention, e.g. performed by the control unit 14, for determining quality measures of plant materials. As shown, this technique includes providing spectrometric data of a region of a plant material 1010 and providing image data 1020 of the same region of the plant material from which the spectrometric data is acquired. As indicated above, the spectrometric data may be optical reflection, absorption and/or transmission spectra (e.g. visible light, NIR) of predetermined wavelength range, Raman spectrum or spectral data acquired by any other spectrometry technique. The image data is typically acquired with visible illumination, but may also include NIR data.

The technique further includes processing and analyzing of the spectrometric data and image data, in accordance with a database containing data (so-called "weighting functions") describing relation between spectrometric response and structural parameter(s) (e.g. density of selected structures, such as trichomes in the plant material). Accordingly, the spectrometric data is processed 1030 for determining spectral traces of the selected active materials (e.g. selected cannabinoids such as HTC, CBD etc.) based on pre-stored spectral data. Additionally, the image data is processed 1040 for determining selected one or more structural parameters of the plant material. Such structural parameters may include density and/or size distribution of selected structure of the plant that are known to be associated with the selected active materials. As indicated above, in the non-limiting example of cannabis plants, the selected structures are typically trichomes, known to produce and store most of the active cannabinoids.

The data processing and analyzing further includes determining one or more weighting factors 1050 providing corrections to the relations and amounts of the selected active materials determined from the spectrometric data in view of the determined data about structural parameters. The weighting factors may be applied to quantities of selected active materials as identified in the spectrometric data. Alternatively, according to some embodiments, the weighting factors may be applied to the spectrometric data itself prior to determining the active materials based on corresponding spectral traces. Based on the weighting factors, the weighted composition of the active materials is determined 1060, providing data about the identities and amounts of active materials that are present in the inspected plant material. Accordingly, one or more quality measures of the plant material may be determined 1070.

Such quality measure may be indicative of existence of selected active materials and/or relations between quantities of several active materials. For example, in the case of cannabis plant, plant material having higher content of THC over lower content of CBD may be tagged/classified as being suitable for recreational use, while larger content of CBD over lower content of THC may direct/sort the plant material for medicinal use. Additional measures of various materials may provide ranking of plant strength or other measures, as the case may be.

It should be noted that quality measure of the plant material may be indicated (e.g. labeled) on the plant itself (e.g. on the packaging), such that a user may use a code on the package to view detailed data of the plant composition and quality measure. Such indication may be used for collecting data from user about the actual effects of the plant material as used, allowing determining correlation between plant spectrometric data and structural parameters and the effect on users, as will be described in more details further below.

The weighting factors or weighting functions $f_j^s(d)$ for various active materials are typically pre-stored, e.g. in the memory utility 144 or external storage device accessible by the control unit, in the form of a database including data about spectral traces of the selected materials and corrections based on structural parameters (e.g. structures density, size distribution of structure etc.). The database may be determined by various chemometric and machine learning techniques utilizing analytical data about material compositions and relations of spectral response and structural parameters of the plant material.

Reference is made to FIG. 4 exemplifying a technique for creating such database, i.e. generating data about weighting factors for determining active material contents from spectrometric data and image data according to some embodiments of the invention. As shown is FIG. 4, the data may be experimentally collected and processed by chemometric and machine learning techniques as follows. The technique includes providing a sample set of plant materials (plant material elements, e.g. specific flowers) for data collection 2010. The sample set is used for collection of data pieces including image data 2020, spectrometric data 2030, as well as analytical data about actual content of active materials 2040. The actual active material content of the plant elements in the sample set may be determined by any analytical tool, such as HPLC or other technique, for determining actual content of the active materials 2050. Additionally, the image data is processed for determining structural parameters 2025 of the plant material. As indicated above, such structural parameters are typically selected in accordance with data about production and storing of the active materials in the plant material (e.g. trichomes in cannabis plants) and may include data about density of the selected structures, size distribution, color of the structures etc.

The spectrometric data is processed 2050, in combination with the structural parameters determined from the image data 2060 or separately, for determining predicted content of the active materials in the plant material for the sample set. The data about predicted content is correlated with the known data collected by analytically measuring material content of the plant material 2070. Based on the correlations, the weighting function (weighting factors) $f_j^s(d)$ may be determined 2080 for the selected active materials j, corresponding spectrometric (e.g. NIR and/or Raman spectrum) traces s, and structural parameters (e.g. density) values of selected structures (e.g. Trichomes) of the plant material d.

The correlation may be determined employing chemometric and machine learning technique in order to establish a precise correlation and weighting function. Once a sufficient sample set providing spectrometric data (e.g. NIR or Raman spectra) and image analysis data is obtained and correlated with the HPLC analysis of cannabinoids, this can be used to construct a database to be used by machine learning programs to generate weighting function based on structure parameters/density and spectral data.

In this connection, it should be noted that machine learning is a discipline for generating algorithms for implementing statistical methods on computers. It has strong ties to mathematical optimization, which delivers methods, theory and application domains to the field. Machine learning is employed in a range of computing tasks where designing and programming explicit algorithms is not feasible. Example applications include spam filtering, optical character recognition (OCR), search engines and computer vision.

Machine learning and pattern recognition can be viewed as two facets of the same field. When employed in industrial contexts, machine learning methods may be referred to as predictive analytics or predictive modeling.

There are many software tools are used as machine learning tools including, for example, the following tools: dlib, ELKI, Encog, H2O, Mahout, mlpy, MLPACK, MOA (Massive Online Analysis), ND4J with Deeplearning4j, NuPIC, OpenCV, OpenNN, Orange, PyMC, R, scikit-learn, scikit-image, Shogun, Torch (machine learning), Spark, Yooreeka, Weka, KNIME, RapidMiner, Amazon Machine Learning, Angoss KnowledgeSTUDIO, Databricks, IBM SPSS Modeler, KXEN Modeler, LIONsolver, Mathematica, MATLAB, Microsoft Azure Machine Learning, Neural Designer, NeuroSolutions, Oracle Data Mining, RCASE, SAS Enterprise Miner, STATISTICA Data Mine, and TensorFlow.

Additionally, various chemometric techniques and programs utilize NIR spectral data of measured samples together with independent analytical quantitative data derived from HPLC and/or GC analysis. The advantage of HPLC is the ability to detect and quantify both free and acid forms of cannabinoids such as THCA, THC, CBDA and CBD. GC can determine only total/potential THC and CBD but is useful for detection of monoterpenes which are found in lower concentrations, yet may contribute to the overall quality of the cannabis flower.

It should be noted that the use of pre-prepared database may generally be required, as spectrometric response, including NIR and/or Raman spectrum, typically originates from combination and overtone vibrations, the spectra have broad and often overlapped features that require the use of chemometric methods for extraction of information from the data.

For example, a database for spectral trances of selected cannabinoids is prepared by the inventors of the present invention from a set of 58 different samples of cannabis flowers as follows. The cannabis grounded flower are measured by collecting near infrared (NIR) spectrum from distances of 2, 4 and 6 mm Amount of cannabinoid (e.g. in weight percent % w/w) per sample were acquired by HPLC. The collected data is processed by selected algorithms for providing data on preprocessing spectrum and chemometric algorithm.

The so-collected data about spectrometric response and material contents is processed using Partial Least Squares Regression (PLSR) and Principal Components Regression (PCR, also known as Principal Component Analysis (PCA)) techniques providing two multivariate method that treat the spectrum as co-linearity, with the assumption that there is a linearity correlation between each different spectrum. The spectrometric data was correlated with the HPLC acquired data using neural network processing to provide a correlation fit between material content predicted from spectral response and the actual content determined by HPLC.

Reference is made to FIG. 5 showing linear correlation determined between the predicted content and the actual content. The presented data shows 70% correlation between the data predicted from spectral data, as is, and the actual measured content together with evaluations on the other 30% correlation (cross validation and test).

Utilizing chemometric approaches and machine learning the present system can generate a higher order correlation between trichome density and NIR/Raman spectral data in order to generate a calibration curve that utilizes trichome density to correct spectral-derived quantities of the active ingredients.

Multivariate data analysis methods are common tools in solving qualitative and quantitative analysis problems. Chemometric techniques such as PLS, PCR, PCA, MCR (multivariate curve resolution) and discriminant analysis have become standard approaches to quickly analyze complex spectral signatures. MCR can be applied to spectral data to extract the spectra of each active ingredient from a mixture or indeed any collection of spectra comprised of spectral contributions from various active ingredient of plant material. In addition, trichomes may be separated manually under binocular using micro-tweezers to separate them from cannabis flower and used for generating spectral data.

As indicated above, the quality value obtained by the technique of the invention, (e.g. by the above-described system 10) can be used to classify the plant material and use the classification data for sorting and/or tagging of the plant material. As is shown in FIG. 1, the system 10 can further include a sorter 22 for sorting plant material 26, e.g. transported on conveyor mechanism 24. Plant material 26 is interrogated via visible camera 12 and spectrometer/imager 16 (or hyperspectral imager 18) and sorted via sorter 22 based on a quality value thereof. System 10 can further include the weighing station 28 for weighing each plant material sample. The weight information can be used to calculate a % weight of each active ingredient in the sample in order to further classify the plant material according to concentration of active ingredient(s). The quality value of the plant material can reflect quantity or % weight or both. The quality value need not be absolute for each class of plant material but can fall within a discrete range of values characterizing a specific class. Any number of classes can be used from several classes (3, 4, 5, 6 . . . 10) to several dozens or hundreds of classes depending on the plant material and the type of classification (medicinal, nutritional etc.).

As mentioned above, the non-destructive classification provided by the technique of the present invention enables tagging/labeling of specific plant material element(s) and providing the tagged/labeled plant material element(s) to users. This enables collection of large volumes of data and determination of various additional correlating factors between features of spectroscopic data and/or the determined structural parameters of the plant material, and effects of the plant material on users.

In this connection reference is made to FIG. 6 illustrating, in a way of flow chart, an example of a technique of the invention for determining and identifying features of plant related data 6060. The technique may generally be operated as a computer software running on a server system. Further, the different actions may vary in order, in accordance with the different embodiments.

As shown in FIG. 6, the technique is based on creation of a database (step 6010) in which data about each plant material (or plant material element) is recorded. This data is collected/determined by the above described system and method, and includes spectrometric data and one or more structural parameters for each specific plant material element (such as flower). The so-classified plant materials (e.g. flowers) are labeled/tagged in accordance with the classification data 6020. Such labeling/tagging data may include the above described quality measure(s) indicating data about content of active material(s), and may also include data about the raw plant data (spectroscopic data and structural parameters) defining said quality measure(s). Such label/tagging data may include a link enabling the user to access data about the plant material in hands, and to provide/supply data about user effects using said link 6030.

For example, the labels on plant materials may be in the form of Quick Response (QR) codes including link data directing the user to an information source accessible via a communication network (e.g. Internet page) associated with the server and configured for providing (allowing access to) plant material data for users and collecting corresponding user related data, as described more specifically further below.

Generally, when accessing such Internet page, a user may view data about the specific plant material, and may be asked to provide user related data including data about effects of the plant material element on the user and possibly also include user identification data. To this end, the user may be asked to fill out a questioner and/or provide activity data, e.g. collected by accelerometers which may be installed in a hand held electronic unit such as smart phone.

Such user data, typically collected from a plurality of users is provided to the server 6040 where this data undergoes processing and analysis. Generally, each data piece of user related data is associated with a corresponding plant material data relating to the specific plant material element consumed by the user at the corresponding time period. The server (generally, data processor and analyzer) is operable for processing of these data for correlating user related data and plant related data 6050. The processing may utilize cluster analysis, machine learning tools, or any other technique(s) for correlating and identifying relations between various plant material parameters and user related parameters to thereby identify features of the plant related parameters 6060 associated with specific effects or indications of users.

Such processing and correlation between plant related data and user related data may be used for updating the database relating to the analysis of the spectrometric data and the structural parameters of the plant material. For example, certain materials showing undefined traces in the spectrometric data may be found to have desired or undesired effects on users. In that case, the quality measures determined for plant material may be updated to provide better accuracy. Additionally or alternatively, the plant material database may be updated 6070 to include so determined data about plant features and corresponding effects on users.

Further reference is made to FIG. 7 exemplifying a technique for generating and updating plant material database in accordance with user related data collected as described above. To this end, the technique includes providing plant material database 7010, e.g. generated by inspecting and processing a plurality of plant materials as shown in FIGS. 4 and 5, providing user related data 7020, determining plant material features associated with specific desired or undesired effects on users 7030 and generating updated plant database accordingly 7040.

As indicated above, the plant material database is typically generated by correlating spectrometric and structural data features of a plurality of plant material elements and chemical data determined by analytical analysis of the plant material elements. Such database may be limited by existing knowledge of the active materials of the plant material and may thus be updated in view of actual user related data collected as exemplified in FIG. 6. The plant material data, typically including spectrometric data and structural parameters is correlated with the user data to identify effects associated with specific plant material parameters. Such correlation may, for example, show high correlation between a certain feature (pick) in spectrometric data with corresponding data from user about specific effects. Such specific effects may include increase in appetite, nausea, desire to sleep or lack thereof, etc. Generally, such correlation may affect quality measure(s) of plant materials and/or indications associated with the plant materials.

To this end, the present invention may also provide a server system (e.g. software application installed in the server) connectable to a communication network and configured for storing plant material database in a corresponding storage utility. The server system may be responsive to communication requesting plant material data of one or more specific plant material elements to thereby provide such data and request for corresponding user related data to be stored in user related database is a corresponding storage utility, which may be the same storage utility or a different one.

The server may include a processing utility configured and operable for processing correlation between the plant material data and user related database to determine various correlating factors indicative of plant material features and corresponding user effects. Such processing may be done periodically or initiated by operator command.

In view of one or more correlation factors determined by the processing utility, the server may operate for updating the plant material database. Such updating of the plant material database may include for example: data inductive of spectrometric data feature and correspondence with one or more active materials, variation of quality measures in accordance with specific spectrometric features, correlation function between spectrometric data and one or more structural parameters, relation between certain spectroscopic features and indications for user, relation between spectroscopic features and indication of side effects and other plant material related parameters.

The following describes one specific example of plant material that can be classified by the technique of the present invention.

As is mentioned hereinabove, classification of cannabis according to a type and quantity/concentration of cannabinoids is of value in both medical and recreational applications.

The present technique is particularly suitable for classifying cannabis since it can be used to classify the main product of cannabis cultivation (excised flowers) rapidly and accurately without destroying or modifying the plant material. The cannabis plant material can be derived (excised) from varieties of *Cannabis sativa, Cannabis indica* and/or *Cannabis ruderalis* or hybrid lines of the above.

As indicated above, Cannabis produces several cannabinoids that can be used for classification including, but not limited to CBDA, CBD, CBG, CBN, CBC, $\Delta^8$-THC, $\Delta^9$-THC and THCA.

With reference again to FIG. 1, physical sorting of cannabis flowers can be effected as follows. The cannabis flowers may be placed on conveyor 24 and are transported to the interrogation station (visible camera 12 and spectrometer/spectral imager 16 or hyperspectral imager of optical inspection unit 18) where each flower sample is imaged to identify the trichomes and interrogated via NIR wavelengths from 900-2200 nanometer, or using Raman spectrometry.

Once each flower sample may be qualified (using the spectral data and trichome density information as described above), the sample is optionally weighed and sorted (or weighed following sorting) using a mechanical sorter such as a channel sorter, freefall and a chute-fed sorter, a belt sorter or a single-file inspection system. The sorted samples are then treated, weighted and packaged (under controlled environmental conditions) with barcode and or QR code and specific labeling relating to sample potency (recreational or medicinal potency) as determined from the quality value. The bar/QR code can also include information relating to variety of cannabis, grower, weight, growing conditions, potency and the like.

The spectral data and quality value of cannabis plant material can also be used along with a database of patients/users and disease /disease states to further qualify the potency and effect of the cannabis material.

For example, each specific plant material qualified by the present invention can be tested against a cohort of patients/users and the effects (psychoactive, therapeutic) recorded in a database. The various effects can also be correlated with the mode of delivery of the active ingredients (smoked, vaporized, taken orally) to find out if different modes of delivery affect the potency of the cannabis. This enables personalized medicine which can address specific needs of patients/users.

The database of plant material typed via the present spectral data and/or quality value and/or other typing approaches (DNA fingerprinting, HPLC/GC chemical typing, visual phenotyping, grower name, growing conditions, plant variety or the like) can be correlated with one or more of the following parameters: patients DNA sequence, medical indication/s, clinical symptom/s and/or sign/s, physiologic effect/s, immune response/s, cognition or psychological effect/s and/or human genetic bio-marker/s in patient or user, dosage forms, methods of administration (inhalation, smoking, oral or any other form), administration form related parameters (preparation, level of heat etc.), total dosing, number of doses, timing of doses, absorption site and PK parameters (metabolites in the different body fluids and tissues).

The resulting database of plant material correlated to at least one of the above parameters can be used by caregivers and patients/users to select a cannabis variety or mixture of varieties suitable for personal use.

Parameters such as clinical symptom/s and/or sign/s, physiologic effect/s, cognition or psychological effect/s can be self-reported by the user by using a dedicated smartphone app to scan the bar/QR code on the sample of plant material and fill out a questionnaire which can then be correlated to the specific plant material in the database. Parameters which require clinical testing (e.g. immune response, genetic bio-markers), can be reported by the physician/lab technician. Once each type of plant material is tested against a cohort of hundreds or thousands of users, the database of plant material types tagged with a quality value and/or user/grower parameters as well as chemical analysis results can be generated and cross reference between individual results can be established. Big data analytics (Raghupathi and Raghupathi Health Information Science and Systems 2014, 2:3) can then be used to identify new correlations from cross referenced data.

The system of the present invention can also be configured for obtaining spectral information from a plant material or from structures of interest and correlating the spectral information with the weight or phenotype of the plant material. Such a correlation can be used as a quality measure for the plant material which can be correlated to the user parameters of the database described above.

The present invention can be used to type plant material derived from various other plants. Table 1 below provides several examples of such plants.

TABLE 1

| Plant | Plant material | Structure | Spectral wavelength |
|---|---|---|---|
| Tomato | seed | cotyledon | 500-2500 nm |
| corn | seed | endosperm | 1000-1800 nm |
| Tobacco | seedling | apex | 600-2500 nm |

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non-limiting fashion.

Example 1

HPLC Analysis of Cannabinoids

A short and accurate HPLC/DAD analysis method for major acidic and neutral cannabinoids extracted from cannabis flowers is described. The present approach improves and optimizes on previous HPLC-DAD approaches.

Material and Methods

Chemical and Reagents

Cannabinoid reference standards for CBD, CBG, CBN, $\Delta^8$-THC, THCA were purchased from RESTEK (Bellefonte, Pa.) having ≥98% purity. CBC reference standard was purchased from RESTEK (Bellefonte, Pa.) and was ≥95% purity. CBDA and $\Delta^9$-THC reference standards were purchased from Cayman (Ann Arbor, Mich.) and were ≥95% purity. Methanol purchased from J.T Baker (Center Valley, Pa.) in HPLC grade, Acetonitrile purchased from J.T Baker (Deventer, the Netherland) in HPLC grade, Formic Acid was purchased from Sigma-Aldrich (Steinheim, Germany) and ultrapure water was prepared in house.

Cannabis Samples

Cannabis samples were provides by CANNDOC (Israel) as a trimming flowers from 10 different indoor cultivars. Flowers were supplied in a semi dry condition (8-15% Humidity).

Loss on Dry (LOD) Sample Preparation

Cannabis flowers were ground and weighted. The % LOD was calculated from weight differences before and after drying samples at 70° C. over 3 days. The LOD test carried out on the same day of the Assay samples.

HPLC Sample Preparation

Cannabis flowers were ground, weighted (0.2-0.7 g) and extracted with 10 ml methanol by 15 min vortex and 15 min sonication. Because of the higher concentration of major cannabinoids in each sample, a dilution of 1:100 was needed. The extract was filtered over 0.22 μm PTFE filter and then diluted 1:100 with Methanol. All extracts were stored at −20° C. in dark freezer.

Analytical Method

HPLC analysis carried out by Hewlett-Packard (HP) HPLC system (Agilent technologies, 1200 series) equipped with: solvent pump (G1311A), solvent degasser (G1322A), auto sampler (G1329A) and photodiode array detector (DAD, G13150). Spectra were recorded in 200-400 nm range and the quantitative wavelength was determined as 222 nm. Separation of components was achieved by Waters Cortecs C18 analytical column (2.7 mm, 100 mm×4.6 mm) protected with waters Cortecs C18 guard column (2.7 mm, 20 mm×4.6 mm). Data analysis were performed using ChemStation C.01.05 software. Mobile phases consisted of: A: 0.1% formic Acid/water, B: 0.1% formic Acid/MeOH, C: 0.1% formic Acid/ACN. Initial setting was a mixture of A:C=75:25 (v/v) for 2 minutes, which was linearity increased then to 100% B over 5 min and set for 2 more min Then, the column was set to the original conditions in 0.5 min and re-equilibrated for 7.5 min Total runtime was 17 min, column flow rate was 1.0 mL/min and column temperature set to 25° C. Injection volumes of calibrators, quality control samples and extracted samples were 20 μL, and detection was determined to wavelength of 222 nm.

Method Validation

Linearity: Calibration curves were obtained from standards solution in methanol containing seven concentrations for each cannabinoid from 1-100 μg/mL.

QC samples: Controls sample was performed from a mixture of 8 cannabinoids at 10 μg/mL concentration. QC samples were analyzed every 10 authentic series samples.

Selectivity and specificity were assessed by analyzing blank samples (methanol) and the lowest calibrators.

LOD, LOQ: Limits of detection (LOD) and lower limits of quantification (LLOQ) were defined from averaged data of 7 different calibrations in 6 different dates. The LLOQ was determined as 1 μg/ml as the smallest concentration which provided the % RSD between 2-17% and % Accuracy between ±14-23% which are acceptance limits from the nominal value. Precision and accuracy were calculated by analyzing QC 5-9 times on 6 different days.

Stability: extracts stability tested for 48 days at −20° C.

Quantitation

Cannabinoids contents in the sample are quantified using linear equation for each cannabinoid compound standard based on the peak area vs. standard concentration. The individual cannabinoid content is calculated according to the following equation:

$$W = \left| \frac{C \times V_{sample} \times D}{m_{sample} \times 10^6} \right|$$

where:

W is the Cannabinoid content (% weight)
C is the Cannabinoid concentration (μg/ml)
V is the Sample volume (ml)
D is the Dilution factor
m is the sample mass (gr)

Results

Method Validation

The method was linear in the respective calibration ranges, with correlation coefficient values between 0.99949 and 0.99992. Blank samples showed no interference and all analytes were baseline-separated. Typical chromatogram of calibration is presented in FIG. 8. Typical chromatograms of authentic cannabis extracts are presented in FIG. 9 for CBDA, FIG. 10 for THCA and FIG. 11 for CBDA+THCA cultivars. Calibration is performed daily (FIG. 12) and a QC samples were analyzed every 8-10 samples.

Precision and accuracy data for all analytes are summarized in Table 2 for LLOQ and in Table 3 for QC samples. The QC samples (10 μg/mL) were analyzed and calculated for each analyte and provided values under ±12% within the acceptable range of 15%. Quantitation limits range of cannabis flowers are listed in Table 4.

TABLE 2

Precision and Accuracy for all analytes on QC samples (10 μg/ml).

| | Concentration (μg/ml) | STDEV | RSD (%) | Accuracy (%) | n |
|---|---|---|---|---|---|
| CBDA | 8.93 | 0.25 | 2.81 | ±10.7 | n = 5 |
| CBD | 8.82 | 0.78 | 8.82 | ±11.8 | n = 8 |
| CBG | 9.43 | 0.71 | 7.53 | ±5.7 | n = 8 |
| CBN | 9.49 | 0.64 | 6.69 | ±5.1 | n = 8 |
| $\Delta^9$-THC | 8.90 | 0.75 | 8.48 | ±11.0 | n = 8 |
| $\Delta^8$-THC | 8.81 | 0.65 | 7.38 | ±11.9 | n = 9 |

TABLE 2-continued

Precision and Accuracy for all analytes on QC samples (10 μg/ml).

| | Concentration (μg/ml) | STDEV | RSD (%) | Accuracy (%) | n |
|---|---|---|---|---|---|
| CBC | 9.51 | 0.56 | 5.86 | ±4.9 | n = 8 |
| THCA | 9.49 | 0.51 | 5.34 | ±5.1 | n = 8 |

TABLE 3

Precision and Accuracy for all analysts for LLOQ samples (1 μg/ml).

| | Concentration (μg/ml) | STDEV | RSD (%) | Accuracy (%) |
|---|---|---|---|---|
| CBDA | 0.77 | 0.09 | 11.68 | 23.17 |
| CBD | 0.85 | 0.09 | 10.17 | 14.85 |
| CBG | 0.82 | 0.02 | 3.03 | 17.89 |
| CBN | 0.78 | 0.10 | 13.33 | 21.79 |
| $\Delta^9$-THC | 0.92 | 0.15 | 16.56 | 14.21 |
| $\Delta^8$-THC | 0.88 | 0.14 | 15.89 | 14.72 |
| CBC | 0.78 | 0.02 | 2.06 | 21.53 |
| THCA | 0.78 | 0.02 | 2.74 | 22.04 |

TABLE 4

Quantitation limits range of cannabis flowers.

| Cannabinoid | pre drying* | post drying** |
|---|---|---|
| CBDA | 0.02-10.95% | |
| CBD | | 0.73-11.92% |
| CBG | 0.21-0.72% | ≤0.96% |
| CBN | 0.12-0.18% | ≤6.62% |
| $\Delta^9$-THC | 0.20-3.62% | ≤14.7% |
| $\Delta^8$-THC | 0.04-0.05% | |
| CBC | 0.03-0.09% | ≤3.88% |
| THCA | 0.44-21.54% | |

*After humidity normalization (8-15%)
**After dry, 3 days on 70° C.

Selectivity

Selectivity and specificity were assessed by analyzing blank samples (methanol) and the lowest calibrators. The compounds selectivity for detection was ensured by retention time determined and HPLC-MS analysis.

Linearity

For all 8 cannabinoids, a seven point calibration curve with the following concentrations was performed: 1, 2.5, 5, 10, 25, 50, 100 μg/mL in methanol (FIG. 10). Calibration samples were run on a daily basis. The regression coefficients for each analyte are listed in the Table 5.

TABLE 5

The regression coefficients for each analyte

| Cannabinoid | $r^2$ |
|---|---|
| CBDA | 0.99990 |
| CBD | 0.99986 |
| CBG | 0.99986 |
| CBN | 0.99986 |
| $\Delta^9$-THC | 0.99992 |
| $\Delta^8$-THC | 0.99986 |
| CBC | 0.99986 |
| THCA | 0.99988 |

Limit of Quantification (LOQ), Limit of Detection (LOD)

Limits of detection (LOD) and lower limits of quantification (LLOQ) were defined from averaged data of 7 different calibrations in 6 different dates. The LOD and LOQ limits were calculated from calibration curves and found to be 0.169-0.439 and 0.563-1.465 respectively, as presents in Table 6.

TABLE 6 calculated LOD and LOQ

|  | LOD | LLOQ |
|---|---|---|
| CBDA | 0.187 | 0.624 |
| CBD | 0.184 | 0.612 |
| CBG | 0.207 | 0.689 |
| CBN | 0.194 | 0.645 |
| $\Delta^9$-THC | 0.193 | 0.643 |
| $\Delta^8$-THC | 0.169 | 0.563 |
| CBC | 0.195 | 0.650 |

A stringent LLOQ was determined as 1 µg/mL which is the lowest concentration which provided the ±23% acceptance limit from the nominal value. LOD was determined as 0.5 µg/ml as the lowest analyte concentration of a sample which was detected by the analysis method but do not comply the method linearity and therefor can't be quantitate as an appropriate value.

Stability

Cannabis flowers extracts stability were tested over 48 days at −20° C. Area measurements showed high stability with precision of ±1.53% for THCA, ±5.66% for $\Delta^9$-THC and ±2.40% for CBDA extract as shows in FIG. 13 and FIG. 14.

Thus, the technique of the present invention for the determination of CBDA, CBD, CBG, CBN, CBC, $\Delta^8$-THC, $\Delta^9$-THC and THCA in cannabis flowers proved to be specific and selective. The LODs and LLOQs were low enough for differentiation of 10 different cannabis cultivars. The method of the invention avoids the problems of decarboxylation and proved to be fast, inexpensive, accurate and precise. Validation process showed sufficient precision and accuracy.

Example 2

NIR Analysis of Cannabis Plant Extract and Material

The feasibility of quantifying THCA, CBDA, THC and CBD in plant material using NIR spectroscopy was tested.

A NIR spectrum of THCA, CBDA, THC and CBD is provided in FIG. 15 and a NIR spectrum of CBA is provided in FIG. 16. FIG. 17 provides a THCA–THC and THCA–CBDA differential spectra which can be used for the identification of these cannabinoids.

Based on the results of the HPLC on cannabis flower extracts and Chemometric calculations, a NIR–HPLC correlation can be obtained. Quantity of THCA and CBDA was estimated from NIR spectrometry measurements, in both whole and ground cannabis flowers (8-15% humidity) in the wavelength band of 900-2200 nm. Quantity of THC and CBD was estimated in both whole and ground cannabis flowers, wet (8-15% humidity) and dry (after 72 hr. drying in 60° C., 0% humidity) in the wavelength band of 900-2200 nm.

Ground cannabis flowers from ten cultivars were measured for THCA in 474 samples from 137 batches. Samples contained 0.4-21.5% THCA. THCA correlation was $r^2$=0.94, RMSE=0.99 and err<20%=82%.

Whole cannabis flowers from ten cultivars were measured for THCA in 492 samples from 246 batches. Samples contained 0.3-16.5% THCA. THCA correlation was $r^2$=0.89, RMSE=1.48 and err<20%=64%.

Ground cannabis flowers from two cultivars were measured for CBDA in 110 samples from 32 batches. Samples contained 2.5-9.8% CBDA. CBDA correlation was $r^2$=0.92, RMSE=0.58 and err<20%=93%.

Whole cannabis flowers from two cultivars were measured for CBDA in 132 samples from 66 batches. Samples contained 2.3-10.95% CBDA. CBDA correlation was $r^2$=0.77, RMSE=0.94 and err<20%=84%.

These results for THCA and CBDA indicate that grinding of plant material increases the accuracy of NIR spectroscopy since it increases the homogeneity of the plant material. Since trichomes, the cannabinoid-containing structures on the flower surface, do not cover the entire surface of the flower, the unground material is more heterogenic and any NIR reading therefrom must be weighted or corrected for homogeneity by a factor which relates to the density of the trichomes.

Here;
$\Delta^9$-THC: $\Delta^9$-Tetrahydrocannabinol
$\Delta^8$-THC: $\Delta^8$-Tetrahydrocannabinol
THCA: Tetrahydrocannabinol Acid
CBD: Cannabidiol
CBDA: Cannabidiol Acid
CBG: Cannabigerol
CBN: Cannabinol
CBC: Cannabichromene
LOD: Limit of detection
LLOQ: Lower Limit of quantitation
LOD: Loss on drying
µg: microgram
mL: milliliter
ACN: Acetonitrile
MeOH: Methanol
PTFE: Poly Tetra Fluoro Ethylene
RT: retention time
rt: room temperature
STDEV: Standard deviation
RSD: Relative Standard Deviation
S/N: Signal-to-Noise ratio
QC: Quality control
v/v: volume/volume
NIR—Near Infra-Red It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A system for qualifying plant material, the system comprising:
   an inspection zone;
   a support stage configured to support the plant material in the inspection zone;
   at least one camera configured to acquire at least one image of the plant material in the inspection zone;
   at least one processor configured to receive and analyze the camera image to identify a region of interest containing specific plant structures possessing active components;
   at least one spectrometer configured to acquire a spectrometric measurement of the plant material in the inspection zone; and
   wherein the at least one processor is further configured to facilitate a spectrometric measurement of the specific plant structures identified in the camera image, and to enable output of an indicator of a quality measure of the plant material based on the spectrometric measurement of the specific plant structures identified in the camera image.

2. The system of claim 1, wherein the at least one camera includes at least one of a color camera, a greyscale camera, an infrared camera, and a hyperspectral camera.

3. The system of claim 1, wherein the plant structures in the regions of interest include trichomes and wherein the at least one processor is further configured to perform image analysis to enable location of the trichomes in the camera image.

4. The system of claim 3, wherein the at least one processor is further configured to determine trichome density from the camera image.

5. The system of claim 1, wherein the plant material is a cannabinoid, and wherein the at least one processor is further configured to determine at least one of a THC and a CBD measure based on the spectrometric measurements.

6. The system of claim 1, wherein the at least one processor is further configured to determine a correlation between data associated with the at least one image and data associated with the spectrometric measurement.

7. The system of claim 1, wherein the at least one processor is further configured to calibrate the at least one spectrometer using stored predetermined data about the specific plant structures.

8. The system of claim 1, wherein the at least one processor is further configured to identify structural parameters in the region of interest, wherein the region of interest includes a cannabis flower, and wherein the structural parameters include a trichomes distribution in the region of interest.

9. The system of claim 1, further comprising a conveyor for moving the support stage into and out of the inspection zone.

10. The system of claim 9, further comprising a weighting unit along the conveyor for determining weight of plant material.

11. The system of claim 9, further comprising a sorter along the conveyor for sorting the plant material based on determined quality.

12. The system of claim 1, wherein the at least one processor is further configured to output data for physically tagging plant material samples with spectroscopically derived composition information.

13. The system of claim 1, wherein the at least one processor is further configured to perform preprocessing on the camera image to perform at least one of contrast enhancement and edge sharpening.

14. The system of claim 1, wherein the spectrometer is configured with a Near Infra-Red light source configured to interrogate trichomes using a wavelength in a range of 900-2100 nm.

15. The system of claim 1, further including a light source for illuminating the plant material in the inspection zone.

16. The system of claim 1, wherein the at least one processor is further configured to apply at least one weighting factor for providing corrections to amounts of selected active materials determined from spectrometric measurements and stored data about structural parameters.

17. The system of claim 1, wherein the at least one processor is further configured to identify each flower in the camera image and to obtain a spectrographic measurement of each flower.

18. The system of claim 1, wherein the spectrometer includes at least one of an InGaAs device and a Pbs device.

19. The system of claim 1, wherein the at least one processor is connectable to a server and is configured facilitate a spectrometric measurement through association with the server.

20. The system of claim 1, wherein the at least one processor is further configured to conduct the spectrometric measurement without resort to an external server.

* * * * *